(12) United States Patent
Sadakane et al.

(10) Patent No.: US 7,991,107 B2
(45) Date of Patent: Aug. 2, 2011

(54) X-RAY CT APPARATUS

(75) Inventors: Tomoyuki Sadakane, Kyoto (JP); Takahiro Yoshimura, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 107 days.

(21) Appl. No.: 12/215,312

(22) Filed: Jun. 26, 2008

(65) Prior Publication Data

US 2009/0003518 A1    Jan. 1, 2009

(30) Foreign Application Priority Data

Jun. 28, 2007  (JP) ................................ 2007-171173

(51) Int. Cl.
*A61B 6/14* (2006.01)
(52) U.S. Cl. .......................................... 378/39
(58) Field of Classification Search ............ 378/20, 378/39
See application file for complete search history.

(56) References Cited

U.S. PATENT DOCUMENTS

| | | | | |
|---|---|---|---|---|
| 5,995,581 A | * | 11/1999 | Ozaki | 378/20 |
| 2002/0075994 A1 | * | 6/2002 | Shahidi et al. | 378/62 |
| 2002/0122537 A1 | | 9/2002 | Yoshimura | |
| 2002/0154742 A1 | * | 10/2002 | Feldman | 378/191 |
| 2003/0026387 A1 | | 2/2003 | Makila et al. | |
| 2006/0203959 A1 | | 9/2006 | Spartiotis et al. | |
| 2007/0036266 A1 | * | 2/2007 | Kramp et al. | 378/62 |
| 2009/0041191 A1 | * | 2/2009 | Suzuki et al. | 378/98.5 |

FOREIGN PATENT DOCUMENTS

| | | |
|---|---|---|
| JP | 10-225455 | 8/1998 |
| JP | 2000-139902 | 5/2000 |
| JP | 2004-329293 | 11/2004 |
| JP | 2007-144137 | 6/2007 |
| WO | WO 2006109808 A1 * | 10/2006 |

* cited by examiner

*Primary Examiner* — Hoon Song
*Assistant Examiner* — Mona M Sanei
(74) *Attorney, Agent, or Firm* — DLA Piper LLP (US)

(57) ABSTRACT

An X-ray CT apparatus with a function of taking in an X-ray image data obtained by another X-ray apparatus, for use of scout view for a CT for local region of an object to be examined. The apparatus comprises an image data input means for taking in an X-ray image data as obtained by an X-ray detector of another X-ray apparatus by way of such as data importing, together with the attribute information thereon, a display operation means for displaying the X-ray image data as a scout view and receiving the operation of designating an interested area on the X-ray image; and a position control means for relatively moving the object to be examined, relative to the X-ray generator and the X-ray detector, in order to execute a CT for local region of the interested area of the object, based on the operation for the X-ray image displayed as the scout view with the display operation means or the attribute information.

5 Claims, 14 Drawing Sheets

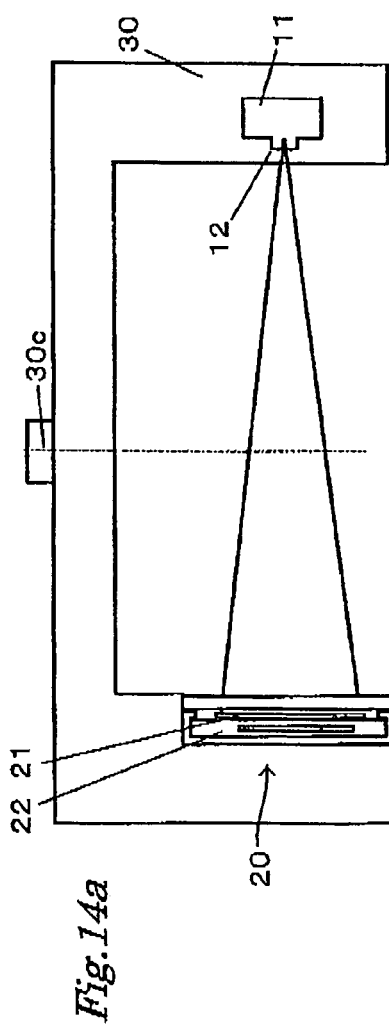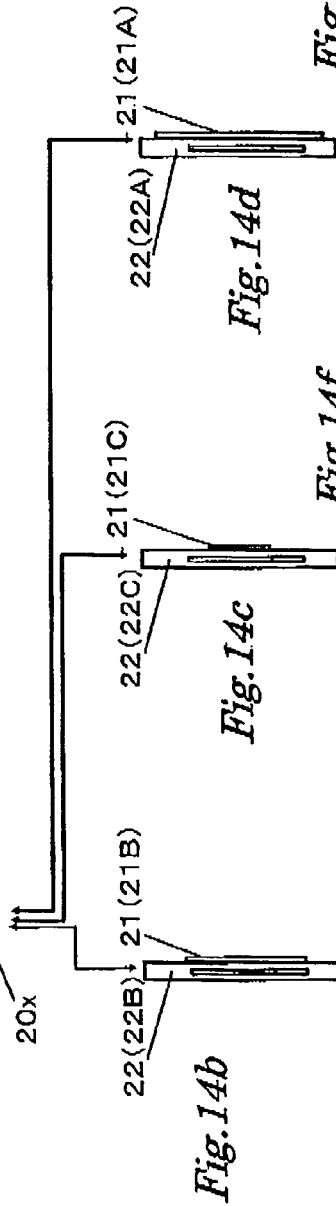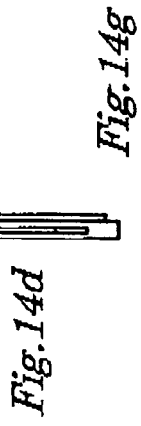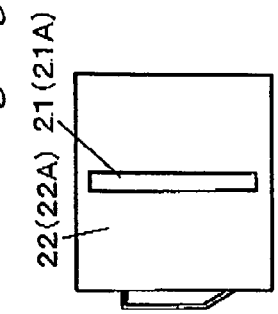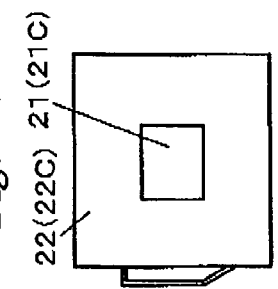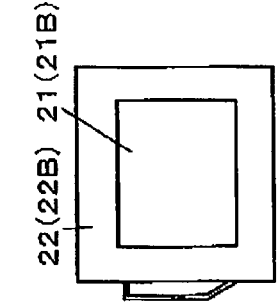

X-RAY CT APPARATUS

BACKGROUND OF THE INVENTION

1. Field of the Invention

The present invention relates to an improvement of an X-ray CT apparatus for executing a CT for local region of an object to be examined, namely a computer tomography for local region of an object to be examined, in which a support means having an X-ray generator and an X-ray detector faced each other is rotated relative to an object to be examined disposed between the X-ray generator and the X-ray detector.

2. Prior Art

When an interested area is designated on a desired position of the maxillofacial area of a patient, specifically a dental arch, and a CT for local region is executed for the designated interested area, a panoramic image of the entire dental arch or a fluoroscopic image as seen in two-direction of the maxillofacial area which is obtained in advance is displayed as a scout view and the interested area can be designated on an X-ray image. As a prior art of such a technology, the following patent document 1 discloses an X-ray CT apparatus capable of obtaining a panoramic image as a scout view by itself.

[Patent Document 1] JP-A-2007-144137

However, when an X-ray CT apparatus capable of a panoramic radiography is introduced as an X-ray CT apparatus for executing a CT for local region in such an environment as a large-scale hospital which already has an X-ray apparatus capable of a panoramic radiography, an X-ray detector for panoramic radiography is provided by these apparatuses, respectively, thereby piling up expenses.

In these days, plural X-ray apparatuses are connected each other by a hospital LAN (LAN inside hospital) in such a large-scale hospital and the X-ray apparatus to be used can receive and display the X-ray image data obtained by other X-ray apparatus via the LAN. However, the X-ray image obtained by other X-ray apparatus cannot be used as a scout view by another X-ray CT apparatus.

SUMMARY OF THE INVENTION

The present invention is proposed to solve the above-mentioned problems and an object of the invention is to provide a newly constructed X-ray CT apparatus in which the X-ray image data of an object to be examined is taken in and the X-ray image is used as a scout view.

According to the first aspect of the present invention, it is characterized in that an X-ray CT apparatus for executing a CT for local region has an image data input means for taking in an X-ray image data of the object together with attribute information thereon, the X-ray image data of the object being obtained by an X-ray detector of another X-ray apparatus, a display operation means for displaying the X-ray image data thereon as a scout view for examination and receiving operation of designating an interested area on the displayed X-ray image and a position control means for relatively moving the object, to the X-ray generator and the X-ray detector, in order to execute a CT for local region of the interested area, based on the operation of designating the interested area and the attribute information.

According to the second aspect of the present invention, it is characterized in that an X-ray CT apparatus for executing a CT for local region has an equipping means detachably equipping an X-ray detector of another X-ray apparatus, a display operation means for displaying an X-ray image data of the object thereon as a scout view for examination and receiving operation of designating an interested area on the displayed X-ray image, the X-ray image data of the object being obtained by the X-ray detector of the another X-ray apparatus, and a position control means for relatively moving the object, to the X-ray generator and the X-ray detector, in order to execute a CT for local region of the interested area, based on the operation of designating the interested area and the attribute information.

According to the third aspect of the present invention, it is characterized in that an X-ray CT apparatus for executing a CT for local region has an image data input means for taking in an X-ray image data of the object obtained by an X-ray detector of another X-ray apparatus, a display operation means having thereon a specific display area with which the X-ray image data of the object is conformed in its size as a scout view and receiving operation of designating an interested area on the displayed X-ray image, a coordinate processing means for converting a position of the designated interested area on the display area into a three-dimensional coordinate information based on a predetermined converting regulation, and a position control means for relatively moving the object, to the X-ray generator and the X-ray detector, in order to execute a CT for local region of the interested area, based on the three-dimensional coordinate information as converted.

According to the fourth aspect of the present invention, in the X-ray CT apparatus described in the third aspect, the display operation means further receives operation of selecting the converting regulation.

According to the fifth aspect of the present invention, in the X-ray CT apparatus described in the third aspect, the display operation means further receives a zoomable operation for the X-ray image data of the object so as to conform the X-ray image with the display area.

According to the sixth aspect of the present invention, in the X-ray CT apparatus described in any one of the first to the fifth aspects, the scout view is a panoramic image of the object to be examined.

According to the seventh aspect of the present invention, in the X-ray CT apparatus described in any one of the first to the fifth aspects, the scout view is a fluoroscopic image as seen in two-direction of the object to be examined.

In the first aspect of the present invention, the apparatus has a position control means for executing a CT for local region of the interested area wherein the object to be examined, the X-ray generator and the X-ray detector are relatively moved based on the designation of the interested area on the X-ray image taken in another X-ray apparatus and the attribute information imported together with the X-ray image data. The attribute information at least includes necessary information to convert the two-dimensional position of a specific position on the X-ray image data to be imported into the three-dimensional positional coordinate for a CT for local region. Therefore, it has an effect that the radiography position can be accurately determined even when the X-ray image data of the object to be examined obtained by the X-ray detector of an X-ray apparatus other than the present X-ray CT apparatus is used for a scout view.

The attribute information may include the kinds of the image, the size of the image and the type of the X-ray apparatus, and it is preferable to include the radiography information as represented by the identification information of the radiography pattern selected depending on the object to be examined. If the manufacturer of the X-ray CT apparatus and that of the X-ray apparatus to obtain the X-ray image to be a scout view are the same, the attribute information may be a simple code. The X-ray image data and the attribute information may be contained in one file or may be an independent file respectively.

In this specification, the term "another X-ray apparatus" means "the X-ray apparatus other than the apparatus itself".

In the second aspect of the present invention, there provided a fitting means capable of mounting an X-ray detector of other X-ray apparatus, so that the X-ray detector of other X-ray apparatus different from the present X-ray apparatus can be used for obtaining a scout view and the X-ray CT apparatus and other X-ray apparatus are not required to be connected by the hospital LAN. Of course, it is possible to design such that the X-ray image data is imported for a scout view, the X-ray image data being taken in the X-ray detector of the mounted other X-ray apparatus to be stored.

According to the third aspect of the present invention, only the X-ray image is imported and the position of the interested area is converted into the three-dimensional coordinate information following the converting regulation. However, as described in the forth aspect of the present invention, the converting regulation may be selected by operation or a default converting regulation may be always selected. According to this structure, the attribute date of the X-ray image is not required to be imported, so that the X-ray image data obtained by the X-ray apparatus in which necessary attribute information is not obtained can be used as a scout view.

According to the fifth aspect of the present invention, the scaling operation of the X-ray image shown as a scout view is possible, so that the error caused when the positional coordinate of the interested area is converted to the three-dimensional positional coordinate for a CT for local region can be restrained by controlling the scale of the image of the object to be examined even if the scale of the object to be examined is different on the obtained X-ray image.

BRIEF DESCRIPTION OF THE DRAWINGS

FIG. 14a shows a schematic structure of an X-ray detector, FIG. 14b-FIG. 14d show side views of three kinds of cassettes which are exchangeably mounted, respectively, and FIG. 14e-FIG. 14g are a front views of the side views, respectively.

DETAILED DESCRIPTION OF THE INVENTION

An X-ray CT apparatus for executing a CT for local region on an interested area set on the maxillofacial area of a patient, specifically on a dental arch, is explained as an example, however, the object of the X-ray CT apparatus of the present invention is not limited to the maxillofacial area but also to a temporomandibular joint or a labyrinth. In addition, the present invention can be applied to an industrial use such as a nondestructive inspection of resin products, not for a human body.

Embodiment 1

Figure 1:
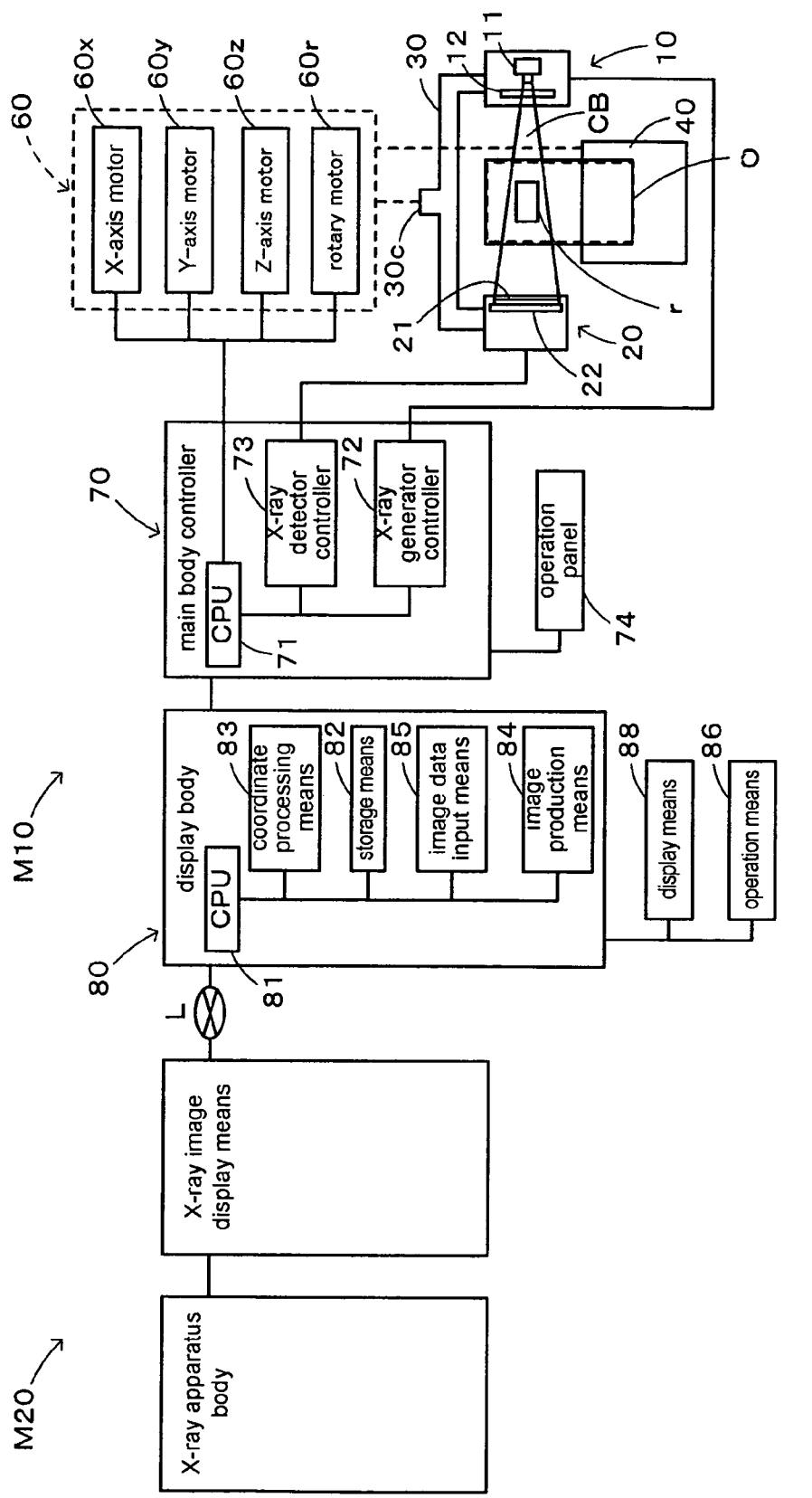
FIG. 1 is a functional block diagram explaining the basic structure of an X-ray CT apparatus employing the present invention.

FIG. 1 is a functional block diagram explaining the basic structure of the X-ray CT apparatus M10 employing the present invention. The X-ray CT apparatus M10 is provided with a main body M11 of the X-ray CT apparatus and an X-ray CT image display apparatus having a function of controlling the main body M11 and displaying the obtained X-ray image.

On the other hand, the X-ray apparatus M20 is provided with a main body M21 of the X-ray apparatus and an X-ray image display apparatus M22 having a function of controlling the main body M21 like the X-ray CT apparatus M10 and is connected with the X-ray apparatus M20 via a hospital LAN.

Line L is a line to connect the X-ray CT apparatus M10 and the X-ray apparatus M20 like the hospital LAN or direct line which connects both of them to import/outport or to input/output data. Line L can be wire line and also can be radio line.

The X-CT apparatus main body M11 has a support means 30 supporting an X-ray generating portion 10 and an X-ray detecting portion 20 faced to each other, an object holding means 40 for holding the maxillofacial area being an object "o" to be examined, a driving portion 60 for driving the support means 30 or the object holding means 40 and a control portion 70 for the apparatus main body. An operation panel 74 is added to the control portion 70. The main body M11 has a function of executing a CT on a part of the dental maxillofacial area following the order from the operation panel 74 or the X-ray CT image display apparatus M12, receives several kinds of orders and the coordinate data from the display apparatus M12 and sends the obtained image data to the display apparatus M12.

Further, as a characteristic of the present invention, the main body M11 has a function of displaying as a scout view for designating an interested area "r" to be rendered to a CT for local region by importing the panoramic image of the entire dental maxillofacial area or fluoroscopic images as seen in two-direction together with the attribute information from an external device like the X-ray apparatus M20. The above-mentioned panoramic image and the fluoroscopic image as seen in two-direction are one example of the X-ray image data. The image may be imported in a form of an electronic signal or in a form of an X-ray image produced on a conventional film or outputted as a hardcopy on a paper. In the latter case, the X-ray image may be scanned by a scanner connected with a computer or a workstation at the X-ray CT image display apparatus M12 and may be converted into an electronic signal to be displayed.

Figure 5:
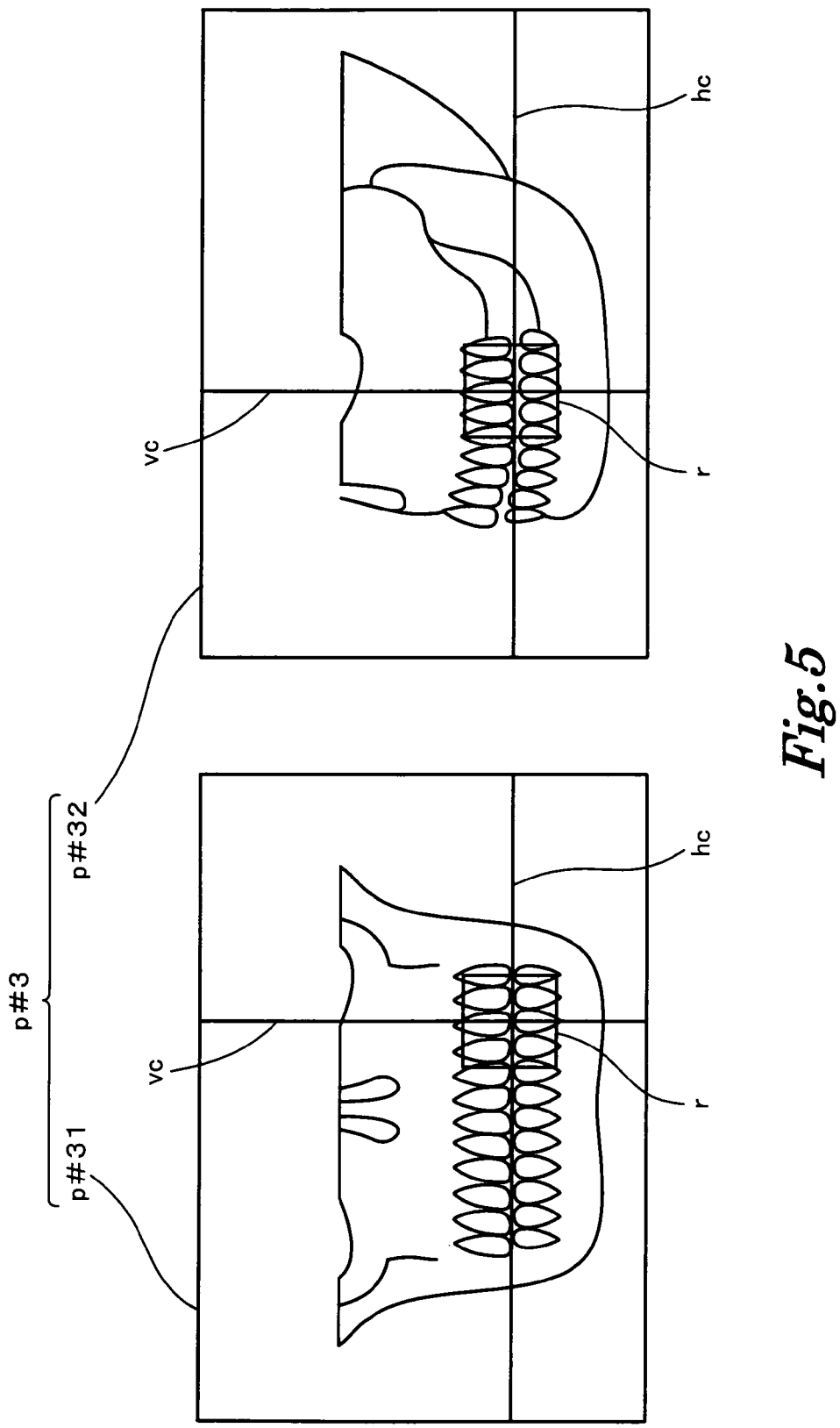
FIG. 5 is an example of a fluoroscopic image as seen in two-direction to be a scout view.

The fluoroscopic image p#3 in FIG. 5 as seen in two-direction comprises an X-ray fluoroscopic image p#31 of the object "o" to be examined obtained when the support means 30 is at a rotary angle of A degree and an X-ray fluoroscopic image p#32 of the object to be examined "o" obtained when the support means 30 is at a rotary angle of B degree, which is different from the angle A. Other fluoroscopic images may be further obtained at different rotary angles and the fluoroscopic images may be those obtained in a plurality of directions more than two directions.

The structure of X-ray CT apparatus disclosed in JP-A-2004-329293, which has been proposed by the present applicant, is one embodiment in which fluoroscopic image as seen in two-direction is used as a scout view.

The X-ray generating portion 10 has an X-ray generator 11 comprised of an X-ray tube for irradiating an X-ray cone beam CB and an irradiation field control means 12 comprised of a slit for regulating the width of the X-ray cone beam CB.

The X-ray detecting portion 20 is constructed as a fitting means detachable with a cassette 22 having a two-dimensionally spread X-ray detector 21 comprised of a CCD sensor. The portion which is mounted on the X-ray CT apparatus main body or the X-ray apparatus main body by being integrated with the X-ray detector 21 and can output the X-ray image data to the X-ray CT apparatus body or the X-ray apparatus main body, like the cassette 22, is called as an X-ray detection unit in the present invention. Therefore, when the X-ray image to be a scout view is obtained by other X-ray apparatus and the cassette 22 storing the obtained X-ray image data is mounted, the X-ray image data or the attribute data can be imported from the cassette 22.

The X-ray detecting portion 20 is not necessarily designed such that the cassette 22 is detachable.

It is only necessarily designed to outport the X-ray image data and the X-ray detector 21 may be fixed to the X-ray detecting portion 20 and may not be detachable.

Further, for example, there may be a case the X-ray apparatus M20 does not have a CT function and the X-ray CT apparatus M10 does not have a panoramic radiography function or a radiography function of the fluoroscopic image as seen in two-direction.

In such a case, the X-ray image data to be a scout view may be obtained by the X-ray apparatus M20, on the other hand, a CT for local region may be executed using the scout view obtained by the X-ray CT apparatus M10.

In the present specification, such an embodiment that the X-ray image data obtained by another X-ray apparatus is taken into an image data input means and imported into the present apparatus is given below as one embodiment of X-ray image data taking-in method.

The driving portion 60 has an X-axis motor 60x and a Y-axis motor 60y for moving horizontally a rotary axis 30c of the support means 30 or the object holding means 40 in a cooperative manner, a Z-axis motor 60z for elevating the support means 30 or the object holding means 40 and a rotary motor 60r for rotating the support means 30. This invention includes a position control means in which the object "o" to be examined, the X-ray generator 11 and the X-ray detector 21 are relatively moved and the interested area "r" being an objective region of a CT for local region is controlled to be positioned at a radiography position being the rotary center of the X-ray generator 11 and the X-ray detector 21.

Such a positioning is executed by moving the rotary axis 30c of the support means 30 in three directions of the X-axis, the Y-axis and the Z-axis.

The embodiment of FIG. 1 shows the structure wherein the driving portion 60 drives both of the support means 30 and the object holding means 40. However, when the Z-axis motor 60z is provided for the support means 30 and the object holding means 40 respectively, two Z-axis motors 60z each are required. In order to eliminate such duplication, when each one of the X-axis motor 60x, the Y-axis motor 60y, the Z-axis motor 60z, and the rotary motor 60r is allocated for either one of the support means 30 or the object holding means 40, the relative movement and the relative rotation of the support means 30 in three directions of the X-axis, the Y-axis, and the Z-axis relative to the object "o" to be examined with the minimum equipment can be achieved.

The first alternative structure 1: The X-axis motor 60x and the Y-axis motor 60y for horizontally moving the rotary axis 30c of the support means 30, the rotary motor 60r for rotating the support means 30, and the Z-axis motor 60z for elevating the support means 30 are provided, but the driving portion for moving the object holding means 40 is not provided.

The second alternative structure 2: The X-axis motor 60x and the Y-axis motor 60y for horizontally moving the rotary axis 30c of the support means 30, the rotary motor 60r for rotating the support means 30, and the Z-axis motor 60z for elevating the object holding means 40 are only provided.

The third alternative structure 3: The rotary motor 60r for rotating the support means 30, the X-axis motor 60x and the Y-axis motor 60y for horizontally moving the object holding means 40, and the Z-axis motor 60z for elevating the object holding means 40 are only provided.

The fourth alternative structure 4: The rotary motor 60r for rotating the support means 30, the Z-axis motor 60z for elevating the support means 30, and the X-axis motor 60x and the Y-axis motor 60y for horizontally moving the object holding means 40 are only provided.

The fifth alternative structure 5: The rotary motor 60r for rotating the support means 30, the Z-axis motor 60z for elevating the support means 30, and the X-axis motor 60x and the Y-axis motor 60y for horizontally moving the object holding means 40 are only provided.

The sixth alternative structure 6: The rotary motor 60r for rotating the support means 30, the X-axis motor 60x and the Y-axis motor 60y for horizontally moving the object holding means 40 and the Z-axis motor 60z for elevating the object holding means 40 are only provided.

There may be the following various alternative structures other than the above.

In the above-mentioned structures 1-6, the object holding means 40 is not rotated and it is preferable because the object "o" does not cause dizziness if it is a human being or animal. However, the object "o" is a material or a machine, the object holding means 40 may be rotated by means of the rotary motor 60r.

Thus the support means 30 having an X-ray generator 11 and an X-ray detector 21 faced to each other is relatively rotated around the object "o" disposed between the X-ray generator 11 and the X-ray detector 21.

In the above-mentioned structures 1-6, a pair of the X-axis motor 60x and the Y-axis motor are provided for either one of the support means 30 or the object holding means 40 and the existing X-Y mechanism is used. However, either one of the X-axis motor 60x and the Y-axis motor 60y is provided for moving the rotary axis 30c of the support means 30 and the other one of them may be used for moving the object holding means 40. Of course, at least either one of the X-axis motor 60s, the Y-axis motor 60y, the rotary motor 60r, and the Z-axis motor 60z may be designed to move both of the support means 30 and the object holding means 40. Otherwise, some of them may be provided for the support means 30, and the other may be provided for object holding means 40.

The main body control portion 70 functions as a radiography control means for controlling a CT for local region and has a CPU 71 for executing several kinds of control programs including a program for controlling the driving portion 60, an X-ray generating portion control means 72 for controlling the X-ray generating portion 10, and an X-ray detecting portion control means 73 for controlling the X-ray detecting portion 20. The operation panel 74 added to the main body control portion 70 comprises a compact liquid crystal panel and a plurality of operation buttons.

The X-ray CT image display apparatus M12 is constructed with, for example, a computer and a workstation and a display apparatus body 80 has the display means 88 comprised of a display apparatus such as a liquid crystal monitor and an operation means 86 comprised of a keyboard and a mouse. The display means 88 and the operation means 86 function as a display and operation means for displaying the X-ray image data imported from the external device such as the X-ray apparatus M20 as a scout view and for receiving the designation operation of the interested area "r" on the displayed X-ray image.

The display and operation means can be called as a display operation means.

Several kinds of commands such as radiography direction can be given by the pointer operation of a mouse on the image or by the character on the display means 88. The display means 88 may be a touch panel and in such a case the display means 88 is also served as the operation means 86.

The display apparatus body 80 comprises a CPU 81 for executing several kinds of programs, a hard disk and so on and has a storage means 82 for storing several kinds of radiography data and images, a coordinate processing means 83 for executing a coordinate calculation, an image producing means 84 for producing a CT image for local region from the CT data for local region, and an image data input means 85 constructed with, for example, a network communication means. The X-ray image data which is to be displayed as a scout view and the attribute information of the object "o" to be examined are imported from the X-ray apparatus M20 and so on via the image data input means 85.

The embodiment of the image data input means 85 is varied depending on the import condition of the X-ray image data.

For example, the CD-ROM reading mechanism of a computer or a workstation is the image data means 85 when the X-ray image data is stored in a CD-ROM, the circuit and the port are the image data input means 85 when the data is imported via a hospital LAN, and a scanner is the image data input means 85 when the X-ray image produced on a film or the X-ray image outputted as a hardcopy on a paper is scanned by the scanner, as mentioned above.

In the present invention, the image data input means 85 also functions as a means for importing the attribute information of the image data, so that the operation means 86 constitutes a part of the image data input means 85 when the attribute information is inputted by operating the operation means 86.

A coordinate calculation means converts the positional coordinate on the X-ray image, displayed as a scout view, of the designated interested area "r" into a three-dimensional positional coordinate for a CT for local region based on the attribute information and determines the objective radiography area for a CT for local region.

The X-ray apparatus main body M21 constituting the X-ray apparatus M20 has a function of obtaining the entire panoramic image or the fluoroscopic images as seen in two-direction of the maxillofacial area of a patient as a characteristic function of the present invention, and the X-ray image display apparatus M22 has a function of controlling the X-ray apparatus main body M21.

The inside structure of the X-ray apparatus M20 is not shown, however, it basically has a similar constituting elements like the X-ray CT apparatus M10. The X-ray apparatus M20 may not have a CT function as long as the X-ray image to be a scout view can be obtained. For example, the apparatus may execute only either one of a panoramic radiography or radiography of the fluoroscopic image as seen in two-direction.

When the X-ray apparatus M20 can execute a panoramic radiography, the X-ray generating portion is designed to irradiates an X-ray slit beam having narrow width for scanning and radiographing the maxillofacial area of the patient. The X-ray detecting portion has the X-ray detector for receiving the X-ray slit beam. The X-ray detector may be formed as a cassette detachable to the X-ray detecting portion. When the X-ray detector is detachable to the X-ray detecting portion, the X-ray detector may be mounted on the X-ray CT main body M11 of the X-ray CT apparatus M10 to be used for radiography as mentioned later.

The X-ray apparatus M20 is only a sample of an external device for exporting the X-ray image data and the attribute information to the X-ray CT apparatus M10. The external device may be an image storage apparatus for aggregating and accumulating the X-ray image data obtained by a plurality of X-ray apparatuses.

The X-ray image exported from the X-ray apparatus M20 includes such kinds of images as a panoramic image and a fluoroscopic image as seen in two-direction. The attribute information may include the kinds of images, the image size and the apparatus type. In addition, it may include the radiography information such as the identification information of the radiography pattern selected for obtaining the X-ray image by the X-ray apparatus M20. Further, the manufacturer of the X-ray CT apparatus M10 and that of the X-ray apparatus M20 are the same, the attribute information may be a simple code. Further, the X-ray image data and the attribute information may be contained in one file or in each independent file.

The panoramic image is obtained while the maxillofacial area of a patient is held at a predetermined position by the object holding means 40, however there is an individual variability between the size and shape of the maxillofacial area, namely and the dental arch DA of the patient. Ideally, it is preferable to set a portion corresponding to the panoramic section of each dental arch, namely a dental arch model dm by understanding the size and the shape of the dental arch DA per a patient, however, it is actually troublesome to measure the dental arch DA per a patient. Therefore, a dental arch with a general shape may be assumed and the portion corresponding to the panoramic section of the dental arch may be set as a general dental arch model dm. If a panoramic radiography is executed assuming the general dental arch model dm, there is no trouble for many person.

Otherwise, variation of a general dental arch model dm may be increased in such a manner that the radiography pattern (the orbit data of the X-ray generator 11 the X-ray detector 21 and the moving speed thereof) optimized for each dental arch model is prepared in advance while assuming a plurality of three-dimensional dental arch models with different size and the most suitable radiography pattern is selected for a patient. In this case, the maxillofacial area of the patient at a predetermined position is radiographed following the selected radiography pattern, so that on thus obtained panoramic image the image of each portion of the dental arch DA is distributed at a position expected in advance, namely a position calculated when the corresponding dental arch model is assumed to be radiographed, even if there may be some error, at the error of the difference of the actual dental arch DA and the dental arch model dm.

Figure 13A:
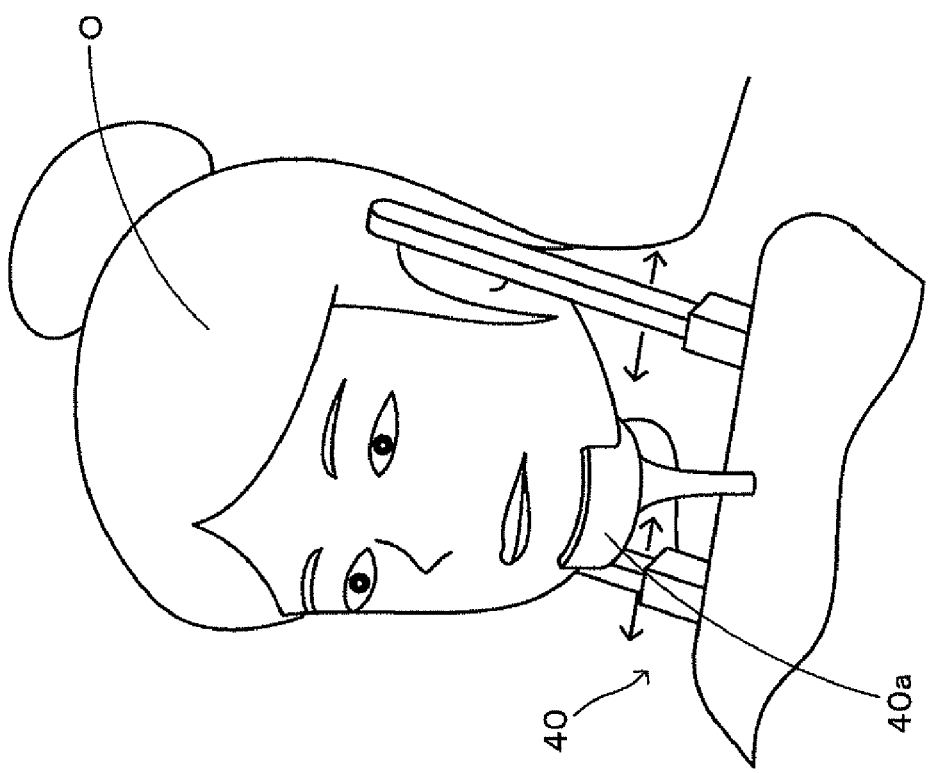
FIG. 13a and FIG. 13b are a perspective view showing the positional relation of an object holding means and an object to be examined and the positional relation of the object holding means and a dental arch model, respectively.
Figure 13B:
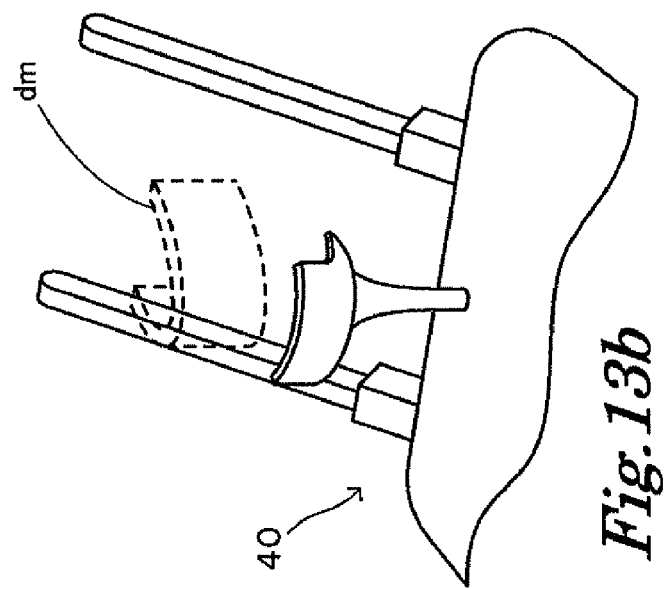

FIG. 13a is a perspective view showing the positional relation of the object holding means 40 and an object "o" to be examined and FIG. 13b is a perspective view showing the positional relation of the object holding means 40 and the dental arch model dm, respectively.

The X-ray generator 11 and the X-ray detector 21 are designed to have a movement orbit capable of radiographing the portion corresponding to the panoramic section of the dental arch of the patient, namely the sectional image of the dental arch model dm, when the jaw of the patient being the object "o" to be examined is placed on the object holding means 40 shown as a chin rest 40a in the figure. Accordingly, the dental arch model dm occupies a static position in the three-dimensional space relative to the object holding means 40. The patient is fixed to the object holding means 40 by placing the jaw on the chin rest 40a as shown in the figure, thereby executing a preferable panoramic radiography. When a panoramic radiography can be executed by the X-ray CT apparatus M10, the position of the panoramic section, namely the dental arch model dm, is specified in the three-dimensional space relative to the X-ray CT apparatus main body M11, so that the position of the dental arch model dm can be understood as the coordinate information of the three-dimensional coordinate.

It is the same in case of X-ray apparatus M20 when a panoramic radiography is executed by the X-ray apparatus M20. In the three-dimensional space where the X-ray apparatus main body M21 is provided, the position of the dental arch model dm for the X-ray apparatus M20 can be understood as the coordinate information of the three-dimensional coordinate.

Figure 2:
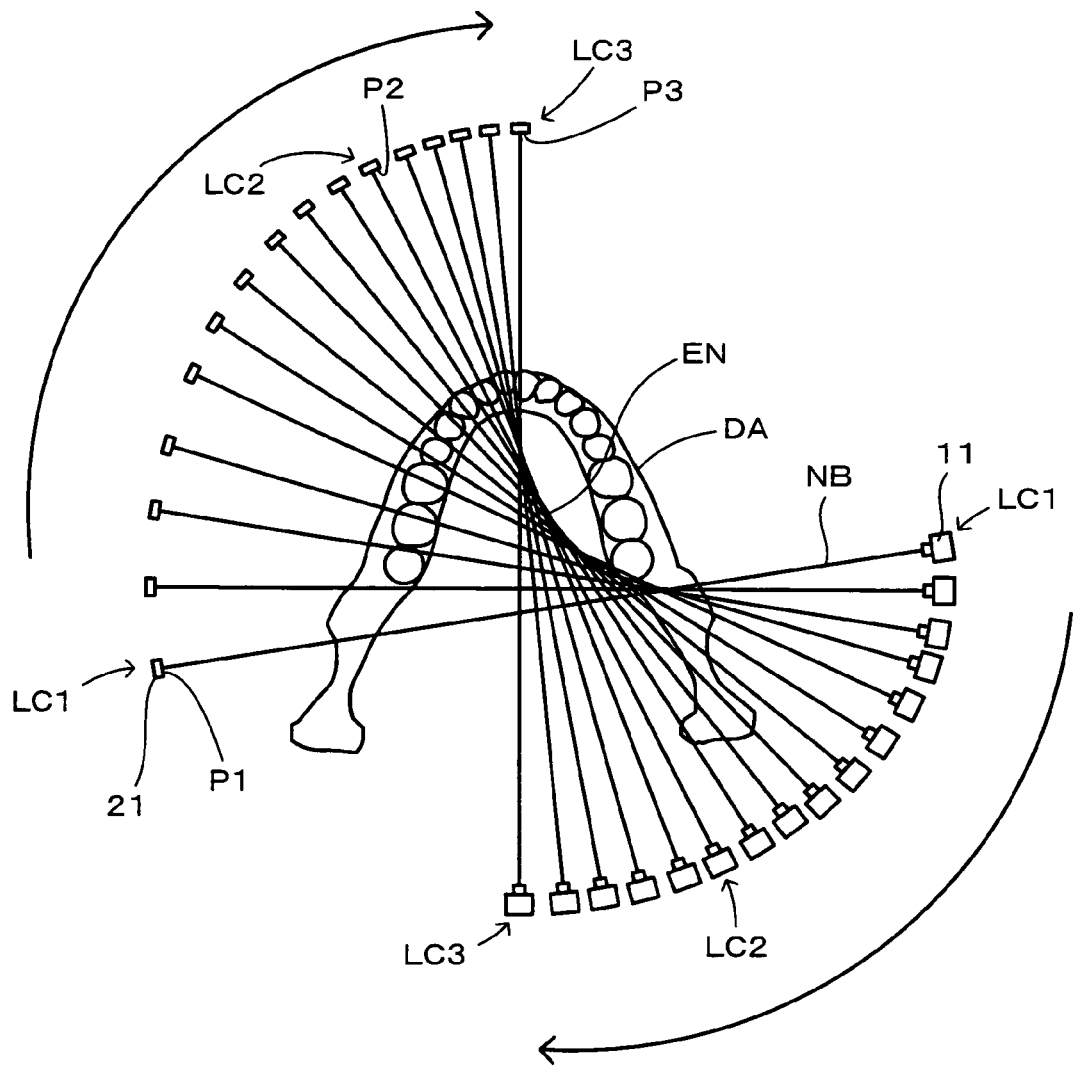
FIG. 2 is a plane view explaining a panoramic radiography method.

FIG. 2 is a plane view explaining a panoramic radiography method. The positional relation of the X-ray generator 11 and the X-ray detector 21 relative to the dental arch DA is changed from LC1, LC2 to LC3, namely from the position for irradiating X-rays on the left jaw P1 through position P2 to the position for irradiating X-rays on the center of a front tooth while the X-ray generator 11 and the X-ray detector 21 are rotated interposing the dental arch DA. A curve EN is an envelope curve drawn by the orbit of the X-ray slit beam NB and the X-ray generator 11 and the X-ray detector 21 rotate around the rotary axis 30c of the support means, namely an extended line 30c1 of the rotary axis 30c to be displaced while interposing the dental arch DA. In case of panoramic radiography, it is required to keep a constant distance between the portion of the dental arch DA to be radiographed, the X-ray generator 11 and the X-ray detector 21 in order to prevent the distortion, so that the rotary center of the X-ray generator 11 and the X-ray detector 21 is sequentially moved while proceeding radiography, but the orbit is different depending on the shape of the dental arch DA. Therefore, when the size and shape of the dental arch DA are different, an individual radiography pattern is required in which the orbit data is optimized per a three-dimensional dental arch model corresponding to each dental arch DA.

Figure 11:
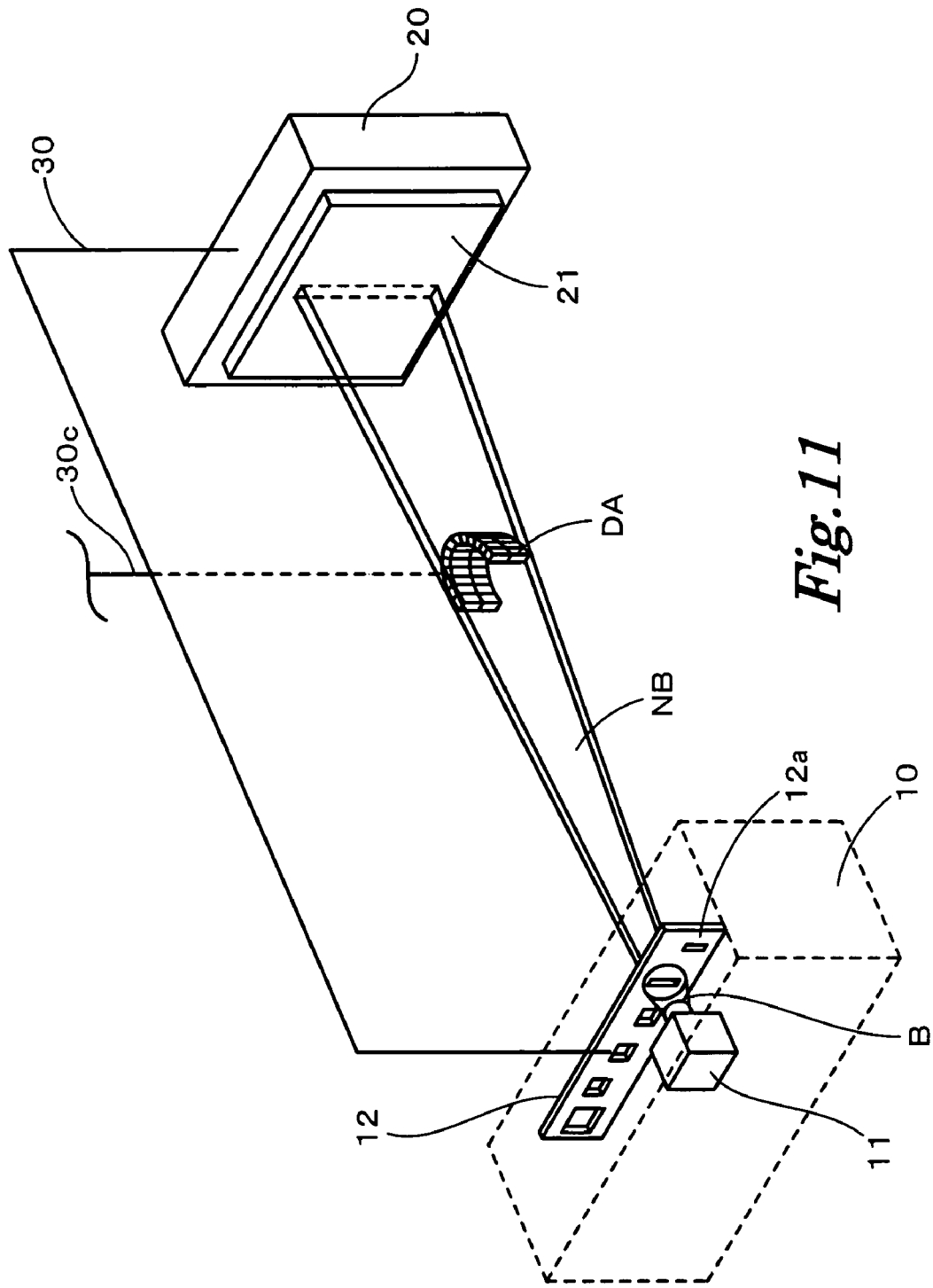
FIG. 11 is a schematic diagram showing a panoramic radiography.

FIG. 11 is a schematic diagram showing a panoramic radiography. The irradiation field control means 12 is provided with different slits for each radiography purpose and is displaced across the X-ray beam B and the slit to be used can be selected. In the figure, an elongate slit for regulating the X-ray beam B into the X-ray slit beam NB is selected. The X-ray slit beam NB transmits through the dental arch DA and is detected on an X-ray detection face of the X-ray detector 21.

As for the fluoroscopic image as seen in two-direction, a radiography pattern optimized for the shape is prepared in advance for each one of plurality of dental arch models and the image of each portion of the dental arch DA is to be spread at an expected position on the fluoroscopic view when an optimized radiography pattern is selected for a patient at the time of radiography.

The X-ray CT apparatus M10 imports the X-ray image data such as the panoramic image and the fluoroscopic image as seen in two-direction and the attribute information exported by the X-ray apparatus M20 and uses the X-ray images as a scout view. The principle of the positioning method for using the imported X-ray image as a scout view is explained hereinafter.

The X-ray apparatus M20 executes radiography based on one or a plurality of dental arch models dm as mentioned above. For example, radiography is executed by selecting the radiography pattern which is optimized for each dental arch model assuming a plurality of dental arch models in which the size is different. When the size and shape of the dental arch model dm used for the X-ray apparatus M20 can be specified by the attribute information, the two-dimensional positional coordinate designating on the image of the dental arch DA on the X-ray image displayed as a scout view can be converted into the three-dimensional positional coordinate (three dimensional coordinate information) for the X-ray CT apparatus main body M11.

The dental arch model dm which is the same as that used in the X-ray apparatus M20 may be introduced into the X-ray CT apparatus M10 and the dental arch DM of a patient may be processed by being represented by the three-dimensional dental arch model specified by the imported attribute information.

Namely, the coordinate processing means 83 qualifies the designation of position into the image of the dental arch DA on the X-ray image displayed as a scout view as the designation of position into the plane image in which a three-dimensional dental arch model is developed or projected two-dimensionally, so that the point of which position is designated is converted into the three-dimensional positional coordinate for the X-ray CT apparatus main body M11 and is specified.

That is, the two-dimensional positional coordinate on the X-ray image of the designated interested area "r" is converted into the three-dimensional positional coordinate for a CT for local region following the converting regulation selected based on the attribute information and is specified.

Figure 7:
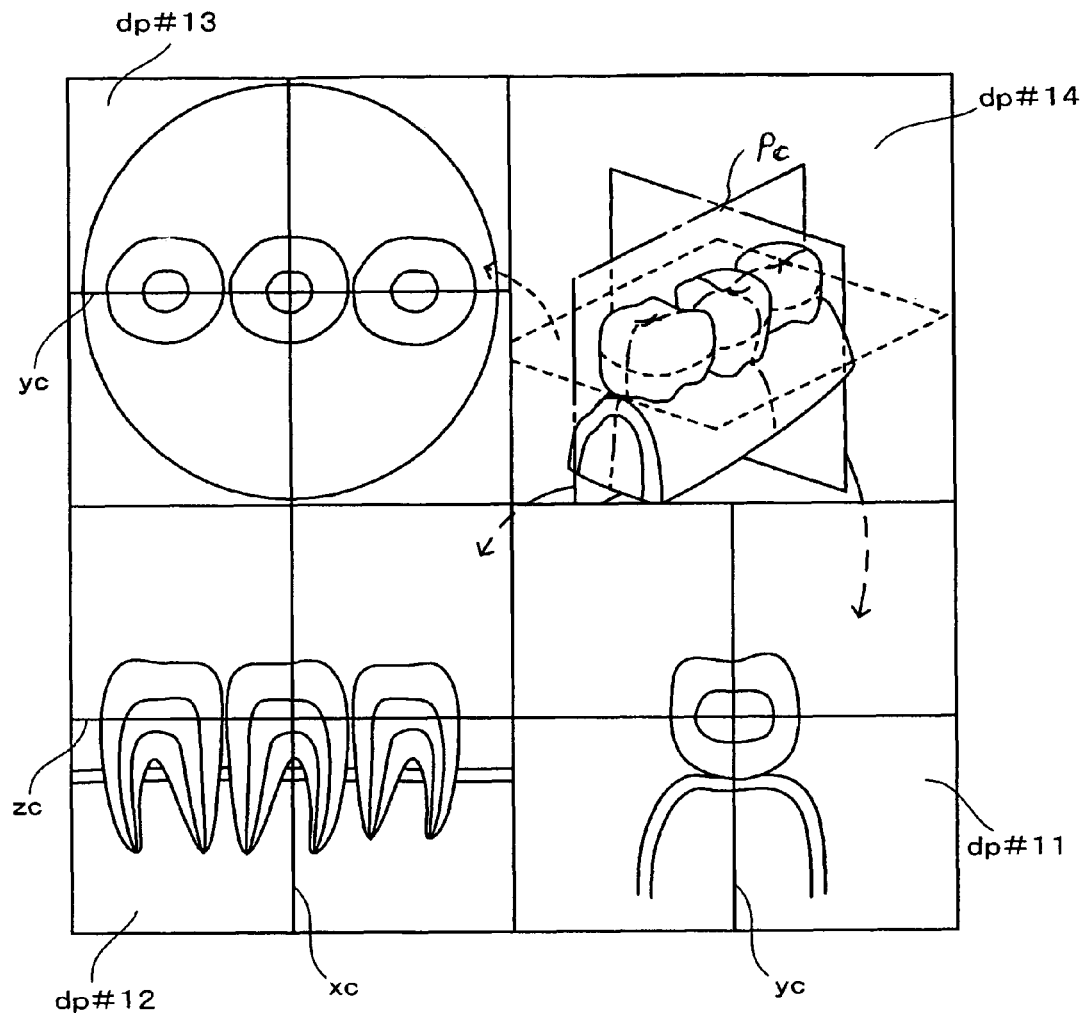
FIG. 7 is an example of a CT image obtained by a method of CT for local region.

Here, the three-dimensional positional coordinate for a CT for local region which is converted from the coordinate of the center of the designated interested area "r" (the coordinate of the point if the interested area "r" is designated as a point) and is specified is shown as a coordinate Pc(xc, yc, zc) in FIG. 7.

The coordinate processing means 83 determines that the objective area for which a CT for local region should be executed, namely the objective radiography area, is around the coordinate Pc (xc, yc, zc). It is preferable that the center of the objective radiography area comes to the coordinate Pc(xc, yc, zc) so as to include the interested area "r" in the objective radiography area.

The support means 30 is relatively moved to the object "o" to be examined and the object holding means 40 by driving the X-axis motor 60x, the Y-axis motor 60y and the Z-axis motor 60z of the driving portion 60, thereby the X-ray generator 11 and the X-ray detector 21 relatively move to the object "o" or the object holding means 40 and come to a starting position for a CT for local region. Next, the X-ray generator 11 and the X-ray detector 21 are rotated around the coordinate Pc (xc, ye, zc) and a CT for local region is executed.

Namely, the support means 30 is positioned by the positioning control of the driving portion 60 which functions as a position control means and a CT for local region is executed for the objective radiography area.

When the same dental arch model dm as that used for the X-ray apparatus M20 is introduced into the X-ray CT apparatus M10, it is converted into the three-dimensional position coordinate on the dental arch model dm of the X-ray CT apparatus M10, however, the converting regulation is unique for a dental arch model, so that it is required to prepare for each dental arch model if the size and the shape of the dental arch model dm are different.

Accordingly, when the converting regulation for converting the two-dimensional positional coordinate of the interested area "r" on the X-ray image into the three-dimensional positional coordinate for the dental arch model is prepared in advance per a dental arch model as function or a reference table, a suitable converting regulation can be selected based on the radiography information contained in the attribute information, namely the identification information of the radiography pattern.

The three-dimensional positional coordinate of the interested area "r" on the dental arch model can be calculated as an offset for the origin set on the dental arch model.

At a preparing stage for a CT for local region, the object "o" is positioned by the object holding means 40 in such a manner that the origin of the dental arch model is set at a predetermined position, in addition, the X-ray generator 11 and the X-ray detector 21 are positioned such that the rotary center thereof comes to the position of the calculated offset.

Figure 12:
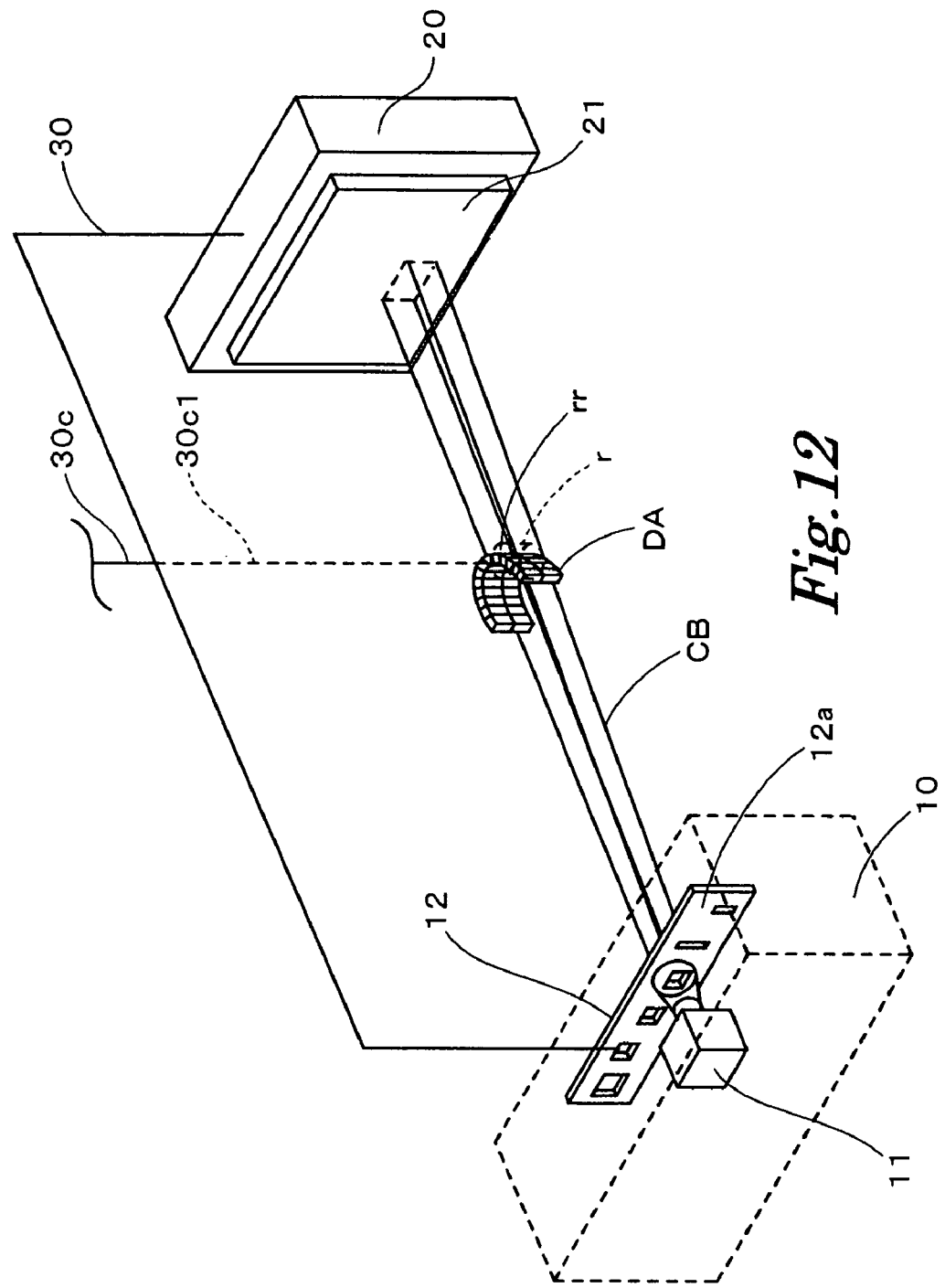
FIG. 12 is a schematic diagram showing a CT for local region.

FIG. 12 is a schematic diagram showing a CT for local region.

In the figure, a square or a substantially square slit is selected to regulate an X-ray beam B into an X-ray cone beam CB.

The X-ray cone beam CB transmits through the dental arch DA and is detected on the X-ray detection face of the X-ray detector 21.

The area (objective radiography area) to be rendered to CT with the X-ray cone beam CB is a substantially tubular area shown with the reference numeral "rr" in the figure. The object "o" to be examined is positioned relative to the support means 30 by driving the X-ray axis motor 60x, the Y-axis motor 60y and the Z-axis motor 60z and a CT for local region is executed in such a manner that the interested area "r" overlaps the area "rr".

In the figure, the square or the substantially square slit for a CT for local region is provided for the irradiation field control means 12 at different heights. The irradiation direction can be changed into a direction parallel to the rotary axis 30c of the X-ray cone beam CB for a CT for local region on the detection face of the X-ray detector 21.

Such a structure enables a CT for local region at different heights in the object "o" to be examined in case of an X-ray CT apparatus wherein the height of the support means 30 relative to the object holding means 40 is not changed.

When the fluoroscopic image as seen in two-direction is used for a scout view, the dental arch model dm is not always required.

It is because the spatial three-dimensional coordinate is specified if there is the two-dimensional coordinate at a specific position designated by one of the fluoroscopic image in two directions and that designated by the other of the fluoroscopic image as seen in two-direction. However, the converting regulation for converting the two-dimensional positional coordinate of the interested area "r" on the X-ray image into the three-dimensional positional coordinate of the X-ray CT apparatus main body M11 is required.

The determination example of the attribute information and the converting regulation are described.

One converting regulation is assumed to be prepared in the X-ray CT apparatus M10 for the panoramic image obtained by the X-ray apparatus M20 and the panoramic image obtained by the X-ray apparatus M20 is assumed to be imported into the X-ray CT apparatus M10. In this case, it is sufficient the attribute information includes that the image is a panoramic image and the used apparatus is the X-ray apparatus M20. In the X-ray CT apparatus M10 the converting regulation is selected based on this attribute information.

If the converting regulation relating to the image obtained by other X-ray apparatus is not prepared in the X-ray CT apparatus M10, when the converting regulation itself is imported as the attribute information together with the X-ray image, the conversion into the three-dimensional positional coordinate is possible based on the imported converting regulation.

Geometric calculation is not always necessary each time of converting into a three-dimensional positional coordinate.

For example, a table may be prepared in which the two-dimensional positional coordinate at the position designated on the scout view and the three-dimensional positional coordinate for relatively positioning the support means 30 for the interested area "r" for executing CT at the X-ray CT apparatus main body M11 side are associated.

In this case, the coordinate of the position designated on the scout view is for example a specific two-dimensional positional coordinate (xa, ya), the support means 30 is controlled and moved in such a manner that the coordinate of the center of the objective radiography area for CT (objective radiography area) becomes a specific three-dimensional positional coordinate like (xa', ya', za') in the X-ray CT apparatus main body M11. Thus, a table is prepared wherein a three-dimensional positional coordinate (xb', yb', zb') is set for a two-dimensional positional coordinate (xb, yb) and a three-dimensional positional coordinate (xa', yb', zb') is set for a two-dimensional positional coordinate (xa, yb) in the same manner.

Next, other structure according to the present invention is explained. In the above-mentioned structure, the X-ray CT apparatus M10 imports the X-ray image data and the attribute information, however, only the X-ray image data may be imported.

According to this structure, the image data input means 85 imports the X-ray image data from an external device, the display means 88 adjusts the X-ray image into a predetermined display area as a scout view and displays it, in other words the X-ray image data is conformed in its size, the operation means 86 receives designation of the interested area "r" for the displayed X-ray image, and the coordinate processing means converts the positional coordinate in the displayed area of the designated interested area "r" into the three-dimensional coordinate for a CT for local region of the object "o" to be examined following the converting regulation selected in advance and determines the objective radiography area to which a CT for local region is to be executed. Then an operator may input the attribute information by means of the operation means 86. In this case, the converting regulation can be selected from the inputted attribute information.

The X-ray CT apparatus M10 may be designed to always use a default converting regulation without inputting the attribute information. In this case, the scale of each part of the dental arch DA on the X-ray image obtained by an optional X-ray apparatus M20 is not uniform, so that it is desirable that the operation means 86 receives a scaling operation that is a zoomable operation of the X-ray image in order that the image of the dental arch DA spreads in a desirable condition in the display area being conformed to the display area. If a reference outline and the like of the jaw bone is overlaid and displayed on the X-ray image in the display area, it can be used as a target for scaling. When the positional coordinate of the interested area "r" is converted into the three-dimensional positional coordinate on the default dental arch model following the default converting regulation in such a manner, the error is expected at the final positioning because of the disagreement of the actual dental arch DA and the dental arch model, however, it does not practically become a big problem as long as the interested area "r" has an adequate field.

Figure 3:
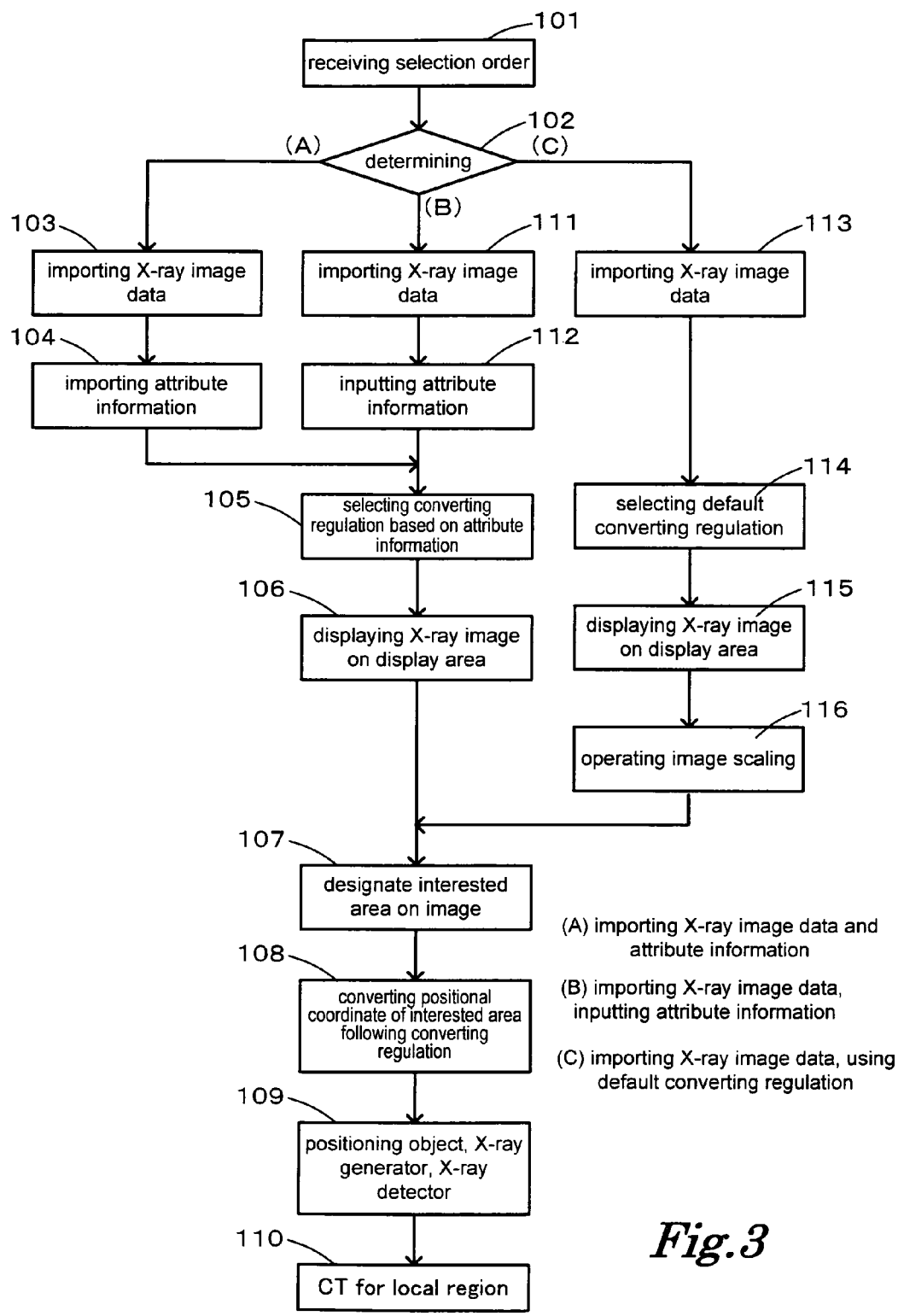
FIG. 3 is a flow chart explaining the procedures for a CT for local region according to the present invention.

FIG. 3 is a flow chart showing the procedures based on the above principle.

The first step receives selection and determines whether it is a process (A) of importing the X-ray image data (step 103) and the attribute information (step 104), a process (B) of importing the X-ray image data (step 111) and inputting the attribute information (step 112), or a process (C) of importing the X-ray image data (step113) and using the default converting regulation (101, 102).

In case of (A) is selected and in case of (B) is selected, they are different in that the attribute information is imported (104) or is inputted (112) and other procedures are common and the converting regulation is selected based on the imported or inputted attribute information (105).

On the other hand, when (C) is selected, it is characteristic in that the default converting regulation is used (114) and the scaling operation for the displayed X-ray image can be executed (116).

Figure 4:
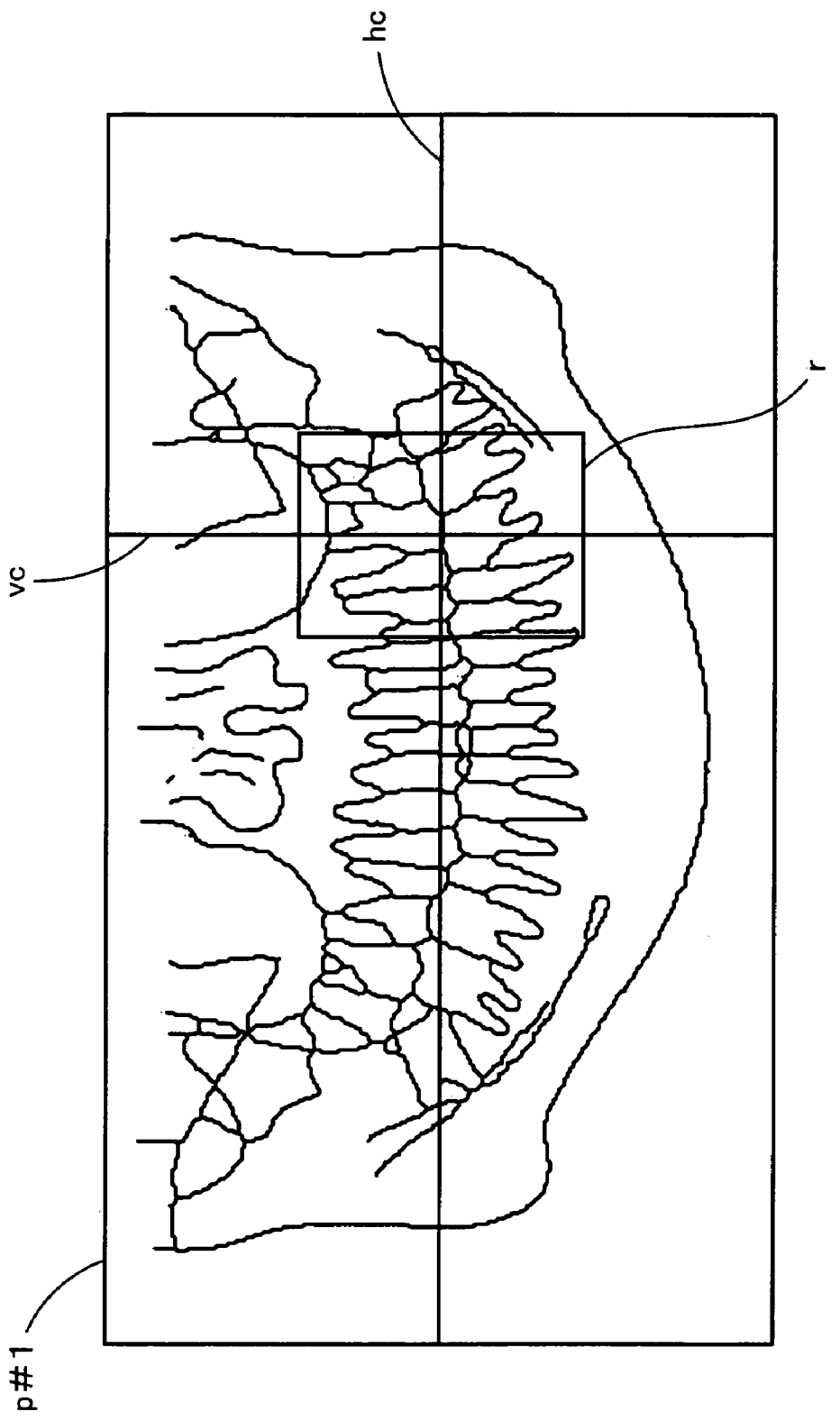
FIG. 4 is an example of a panoramic image to be a scout view.

FIG. 4 is an example of a panoramic image shown as a scout view in the step (106) or (115) in the flow chart and the dental arch DA which is actually curved three-dimensionally is developed and displayed on a plane. A horizontal cursor hc and a vertical cursor vc which move according to the moving operation by an operator are shown on the panoramic image p#1 and the interested area "r" is designated on the crossing position of them. The interested area "r" is shown as a quadrangular frame in this figure, however, it is an outline when the interested area "r" which is actually cylindrical is seen from the side.

When the quadrangular frame is the same or substantially the same as the objective area for CT, the area to be rendered to CT can be checked with eyes, thereby being convenient.

The designation of the interested area "r" is executed (step 107 in Fig.3) by the cursor operation on the displayed image in Fig. 4, however, in other examples, an input means capable of designation for each part of the tooth may be prepared and the tooth which requires a CT for local region may be designated while observing the scout view. For example, while the displayed panoramic image is observed, when it is found that the tooth required for a CT for local region is at the innermost upper right, the code allotted for the innermost upper right tooth in advance is inputted or its switch is turned on.

FIG. 5 is an example of the fluoroscopic image as seen in two-direction shown as a scout view in the step (106) or (115) in the flow chart, a horizontal cursor hc and a vertical cursor vc which move according to the moving operation by an operator are shown on each of the front X-ray transmitted image and the side X-ray transmitted image and the interested area "r" is designated on the crossing position of them. The interested area "r" is shown as a quadrangular frame in this figure which is an outline when the cylindrical configuration is seen from the side, as mentioned above.

It is convenient when the quadrangular frame is the same or substantially the same as the objective area for a CT for local region, as mentioned above.

The designation of the interested area "r" is executed by the cursor operation on the displayed image in FIG. 5, however, in other examples, an input means capable of designation for each part of the tooth may be prepared and the tooth which requires a CT for local region may be designated while observing the scout view, as mentioned referring to FIG. 4.

Figure 6:
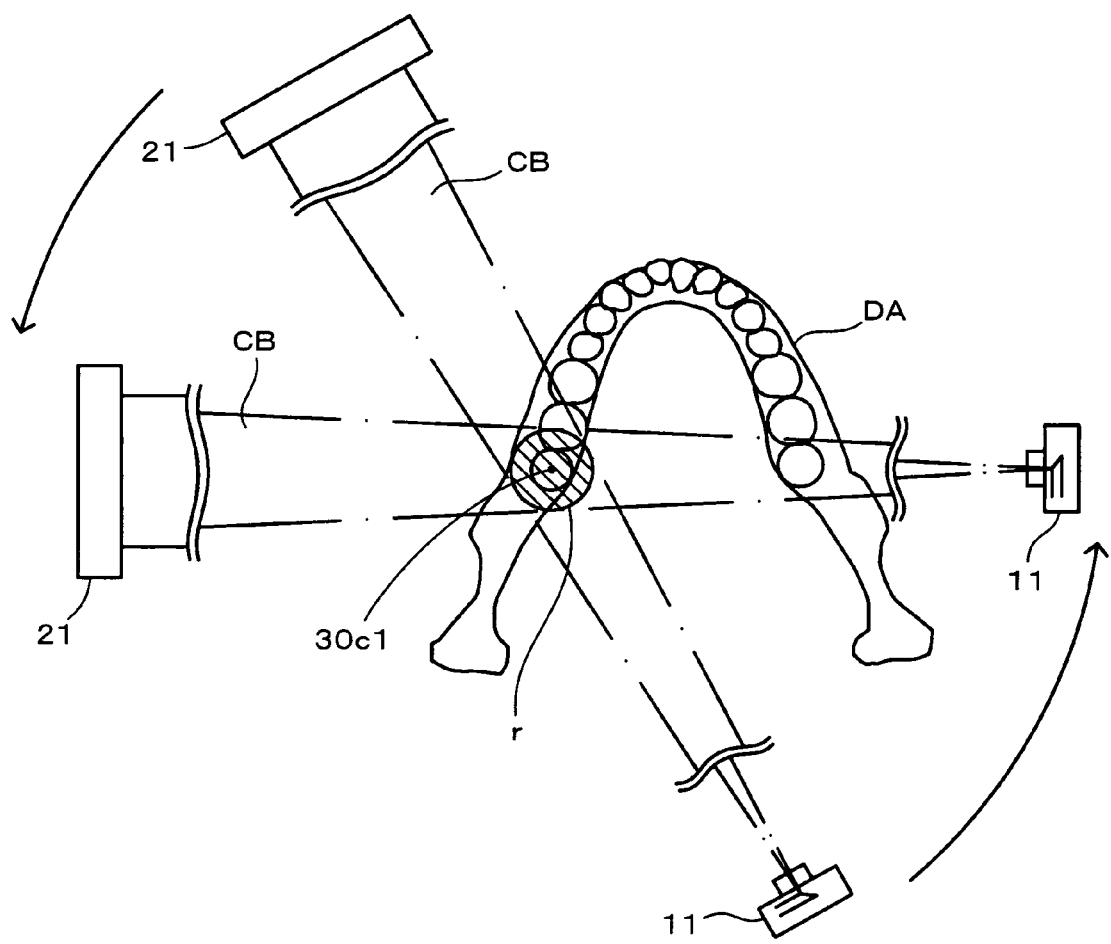
FIG. 6 is a plane view showing a CT for local region method.

FIG. 6 is a plane view showing a CT method for local region executed in the step (110) of the flow chart. The rotary center 30c of the support means 30 is positioned at the step (109) following the three-dimensional positional coordinate converted at the step (108). The X-ray generator 11 and the X-ray detector 21 are rotated around the extended line 30c1 of the static rotary center 30c following the circular orbit during a CT for local region.

A CT for local region (locally irradiating X-ray CT, partial CT) executes CT of a part of the object "o" to be examined wherein a portion to be always irradiated with the X-ray beam, namely the objective radiography area for CT, which is required for reconstruction of a CT image is a part of the object "o". When a portion other than the objective radiography area for CT exists before or after the objective radiography area in an X-ray irradiating direction, the reconstruction of a CT image on the objective radiography area for CT is possible without trouble. The structure for a CT for local region described in JP-2000-139902 and JP-A-10-225455 which are proposed by the present applicant can be used herein.

According to a CT for local region, CT is possible by irradiating X-rays only on a minimum portion of the object "o" to be examined, so that it is advantageous that the exposed dosage amount is remarkably reduced comparing with CT in which X-rays are irradiated on the entire object.

Fig.7 is an example of a CT image obtained by a CT for local region and shows a sectional images of an X section dp#13, a Y section dp#11 and a Z section dp#12 which are orthogonal each other and a volume image dp#14 which are produced from the CT data following the known procedures.

When any one of the cursors zc, yc, zc is operated and moved, the corresponding sectional image is changed into the sectional image at the position where the cursors xc, yc, zc is moved and displayed.

Here the relation of the attribute information and the converting regulation is explained.

There is no fixed form of converting regulation and many regulations are possible. For example, it may be a geometric function or the coordination of a specific position and a specific position like the above-mentioned table.

Of course when the X-ray image data is a panoramic image data and when it is fluoroscopic images as seen in two-direction, the coordinating relation of the two-dimensional positional coordinate at the point or the position designated on the X-ray image and the three-dimensional positional coordinate after conversion is entirely different, so that they have to follow different converting regulation.

If the size and shape of the dental arch DA are the same, the size and shape of the dental arch model dm used by the X-ray CT apparatus M10 and those of the dental arch model dm used by the X-ray apparatus M20 are sometimes slightly different.

Even if the size and shape of the dental arch model dm used by the X-ray CT apparatus M10 and of the dental arch model dm used by the X-ray apparatus M20 are different, the conversion from the two-dimensional positional coordinate into the three-dimensional positional coordinate is possible as mentioned above as long as an appropriate converting regulation is used.

The example in which the size, shape, and position of the dental arch model dm used for obtaining the X-ray image to be a scout view are specified by the attribute information and the converting regulation suitable for the specified dental arch model dm is a typical combination example of the attribute information and the converting regulation.

As understood by the above description, the attribute information is at least information capable of converting the two-dimensional position at a specified position on the X-ray image data to be imported into the three-dimensional positional coordinate for a CT for local region and what is necessary is just to be able to attain the purpose.

The attribute information does not have a specific form and several kinds of information are possible. For example, the radiography pattern may be the attribute information as mentioned above, the shape of the section may be the attribute information or the manufacture number of the X-ray apparatus may be the attribute information.

Panoramic radiography includes several types of radiography for an adult, a child, a temporomandibular joint and the like in which the size, shape and position of the section are different. A code may be allotted for each type and the code which shows the imported X-ray image is what type of panoramic radiography may be imported as the attribute information.

For example, when the sensor used for a panoramic radiography is a CCD sensor for a TDI control, the frequency of a TDI clock and the rotary speed per a rotary angle of the support means (rotary arm) 30 may be the attribute information.

Or the converting regulation itself may be the attribute information as mentioned above.

The basic idea of the above-mentioned structure is as follows.

When the spatial three-dimensional positional coordinate, for example Pm2 (xm2, ym2, zm2), at the X-ray apparatus body M21 of a region op of the object "o" to be examined obtained by the X-ray apparatus M20 is specified, the spatial three-dimensional positional coordinate, for example Pm1 (xm1, ym1, zm1) of the region op at the X-ray CT apparatus main body M11 can be specified when the object "o" is fixed to the X-ray CT apparatus main body M11.

When there is the X-ray image data of the object "o" obtained by the X-ray apparatus M20, if the X-ray image data is a panoramic image, the spatial three-dimensional positional coordinate Pm2 at the X-ray apparatus main body M21 of the region op shown on the X-ray image data can be specified if there are the information of the dental arch model dm used for the radiography in the X-ray apparatus M20 and designation of the two-dimensional positional coordinate on the obtained panoramic image. Or if the X-ray image data is the fluoroscopic image as seen in two-direction, the three-dimensional positional coordinate Pm2 can be specified if there is designation of the two-dimensional positional coordinate on each one of the fluoroscopic images as seen in two-direction obtained by the X-ray apparatus M20.

When the same object "o" to be examined is fixed to the X-ray CT apparatus main body M11, the spatial three-dimensional positional coordinate Pm1 of the region op at the X-ray CT apparatus main body M11 can be also specified, thereby enabling a CT for local region aiming for the coordinate Pm1.

The correspondence of the coordinates Pm2 and Pm1 may be calculated or may be set as a table in advance.

A more specific example of the X-ray CT apparatus M10 utilizing the present invention is explained.

Figure 8:
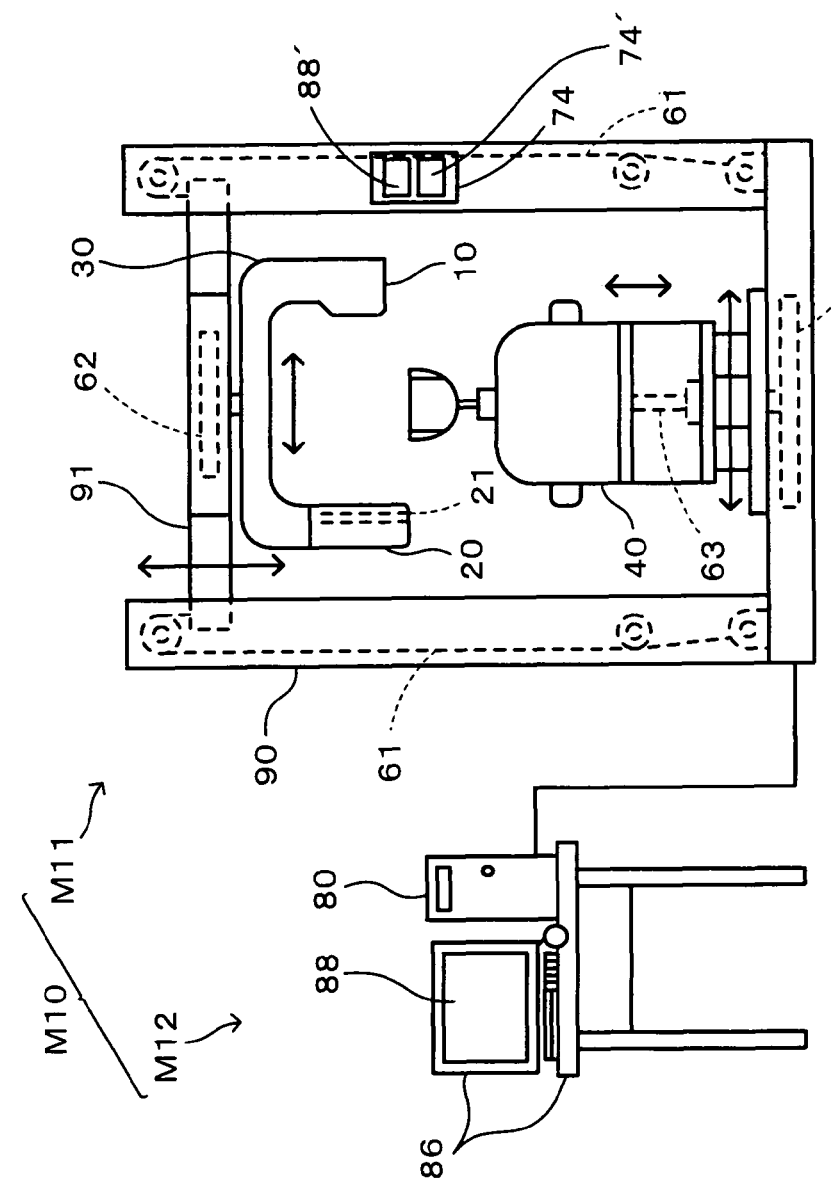
FIG. 8a and FIG. 8b are a front view and a side view of an X-ray CT apparatus applied with the present invention, respectively.

FIG. 8a and FIG. 8b are a front view and a side view of the X-ray CT apparatus M11, respectively. The X-ray CT apparatus body M11 has the support means 30 which is constructed as a rotary arm housing the rotary motor 60r and supports the X-ray generating portion 10 and the X-ray detecting portion 20 at the both ends thereof so as to be faced each other and the object holding means 40 formed like a sheet having a holder for fixing the head of a human body being the object "o" to be examined. The support means 30 and the object holding means 40 are displaceable provided for a fixing frame 90 formed like an arch.

The X-ray CT apparatus M11 is connected with the X-ray CT image display apparatus M12 constituted with a workstation via a communication cable so as to be capable of two-way communication.

The support means 30 is attached to the fixing frame 90 via an elevation frame 91 movable up and down as shown in the vertical arrow in FIG. 8a. The elevation frame 91 includes an XY table 62 for horizontally moving the rotary axis 30c of the support means 30 in back and forth and in right and left as shown in the crosswise arrow in FIG. 8a and FIG. 8b.

The bottom of the object holding means 40 is supported upwardly by means of an elevation means 63 movable up and down as shown with the vertical arrow in FIG. 8a, and the bottom of the fixing frame 90 includes an XY table 64 for horizontally moving the elevation means 63 in back and forth and in right and left as shown with the crosswise arrow in FIG. 8a and FIG. 8b.

A support pillar of the fixing frame 90 is provided with the operation panel 74 including a display means 88' such as a liquid crystal monitor and a compact liquid crystal panel and the input means 74' comprised of a plurality of operation buttons.

The driving portion 60 includes the rotary motor 60r, a chain driving portion 61, the X-axis motor 60x and the Y-axis motor 60y of the XY table 62, the elevation means 63, and the X-axis motor 60x and the Y-axis motor 60y of the XY table 64.

According to such a structure, even if the X-ray image data is obtained by the X-ray detector 21 of the X-ray apparatus M20 other than the X-ray CT apparatus M10, it can be used as a scout view as long as the object "o" to be examined is same.

The mentioned above is an example in which the X-ray image data of the object "o" to be examined obtained by the X-ray detector 21 of the X-ray apparatus M20 other than the X-ray CT apparatus M10 is imported. Next explained is an example the X-ray detector 21 of the X-ray apparatus M20 is attachable to the X-ray CT apparatus M10.

FIG. 14a shows a schematic structure of the X-ray detecting portion 20 provided for the X-ray CT apparatus M10. The X-ray detecting portion 20 is designed to be exchangeably mounted with the cassette 22 constituting the X-ray detector 21.

FIG. 14b, FIG. 14c and FIG. 14d show a side view of three kinds of cassettes 22 which are exchangeably mounted, respectively, and FIG. 14e, FIG. 14f, and FIG. 14g are a front view of the cassettes 22, respectively. The cassettes 22 shown in FIG. 14a -FIG. 14g are one example of the X-ray detector 21.

The X-ray detecting portion 20 is provided with a fitting portion 20x for detachably mounting the cassette 22 having the X-ray detector 21. In the figure, the fitting portion 20x is a mounting means comprised of a groove to which the upper side and the lower side of the cassette 22 are inserted and removed.

A cassette 22A for panoramic radiography having an X-ray sensor (X-ray detector) 21A for a panoramic radiography and a cassette 22B for CT having an X-ray sensor (X-ray detector) 21B for CT are detachable and exchangeable to the fitting portion 20x. The cassette 22B has a detection face much wider than the irradiation field of the X-ray cone beam CB for a CT for local region which is regulated by the irradiation field control means.

The radiography of the above-mentioned fluoroscopic image as seen in two-direction is possible by using the detection face of the cassette 22B.

In case of obtaining the fluoroscopic image as seen in two-direction, the widest square or substantially square slit is selected among the slits 12a of the irradiation control means 12 shown in Fig. 11 and Fig. 12.

Alternative to the cassette 22B, a cassette 22C only for a CT for local region having an X-ray sensor (X-ray detector) 21C having a narrow detecting face which is substantially same as the irradiation field of the X-ray cone beam CB for a CT for local region may be mounted.

The X-ray CT apparatus M10 can execute a panoramic radiography using the cassette 22A for the X-ray CT apparatus M10, but it can also execute a panoramic radiography by equipping a cassette 22A' (not shown) for a panoramic radiography for the X-ray apparatus M20. Or it may be designed so as to obtain the fluoroscopic image as seen in two-direction by mounting a cassette 22B (not shown) for obtaining the fluoroscopic image as seen in two-direction having a wide detection face for the X-ray apparatus M20.

Figure 10:
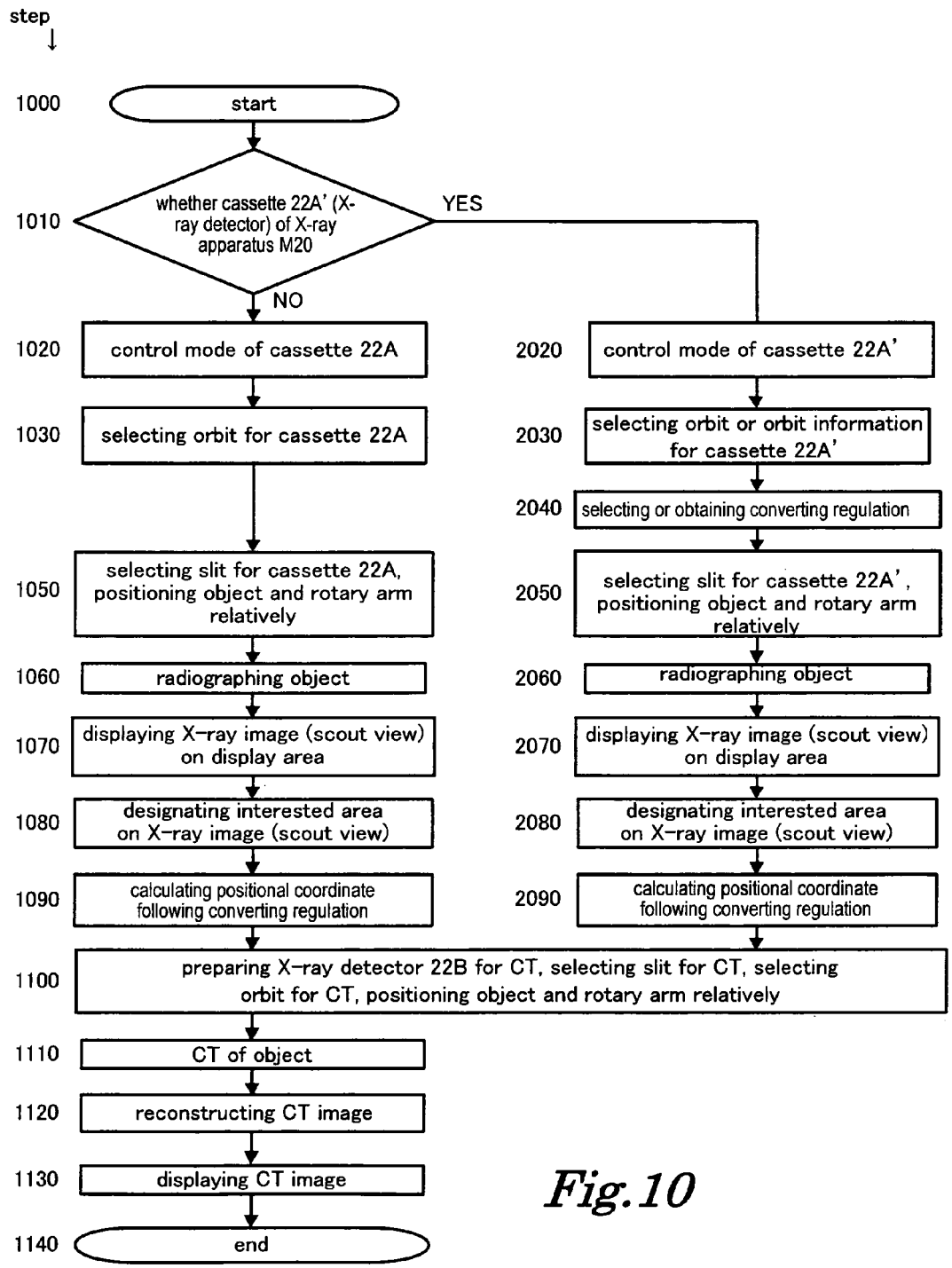
FIG. 10 is a flow chart showing the procedures according to an embodiment capable of mounting an X-ray detector for other X-ray CT apparatus.

FIG. 10 is a flow chart specifically showing procedures wherein the X-ray detecting portion 20 of the X-ray CT apparatus M10 is capable of mounting the X-ray detector 21 for the X-ray apparatus M20.

The procedure is branched whether the X-ray detector for the X-ray CT apparatus M10 is mounted or the X-ray detector for the X-ray apparatus M20 is mounted, as shown in the step (1010). The X-ray detector 21 is provided for the cassette 22, so in case of using a panoramic image for a scout view, the procedure is branched whether the cassette 22A is equipped or the cassette 22A' is equipped. In case of using the fluoroscopic image as seen in two-direction used for a scout view, it is branched whether the cassette 22B is equipped or the cassette 22B' is equipped.

In the flow chart in the figure, a panoramic image is assumed to be used as a scout view and the procedure is branched whether the cassette 22A is mounted or the cassette 22A' is equipped.

The cassette 22 may be equipped manually or may be automatically equipped by means of a feeding mechanism and the like (not shown).

The process starts at step (1000) and ends at step (1140). At the steps (1020), (2020), the control mode is selected depending on which cassette 22 is equipped.

At the step (1030), the orbit for a panoramic radiography by the cassette 22A is selected, for example the movement orbit of the X-ray slit beam NB or the movement orbit of the X-ray generator 11 and the X-ray detector 21.

At the step (1050), the slit for a panoramic radiography is selected so as to execute a panoramic radiography with the cassette 22A and the object "o" to be examined and the support means (rotary arm) 30 are relatively positioned.

At the steps (1060), (1070), a panoramic radiography is executed and the panoramic image is displayed.

The panoramic image is shown on the display means 88 and so on as a scout view.

At the step (1080), an operator designates the interested area "r" on the displayed panoramic image.

At the step (1090), the positional coordinate of the interested area "r" is calculated following the converting regulation prepared for the panoramic image obtained by the cassette 22A.

At the step (1100), the cassette 22B is mounted for a CT for local region.

The cassette 22 may be mounted manually or may be automatically mounted by means of a feeding mechanism and the like (not shown). The slit is selected for a CT for local region.

The orbit for a CT for local region by the cassette 22B is selected, for example the movement orbit of the X-ray cone beam CB or the movement orbit of the X-ray generator 11 and the X-ray detector 21.

The object "o" to be examined and the support means (rotary arm) 30 are relatively positioned so as to execute a CT for local region of the interested area "r" with the cassette 22B.

At the steps (1110), (1120) and (1130), a CT for local region, image reconstruction and display are executed.

On the other hand, at the step (2030), the orbit for panoramic radiography by the cassette 22A' is selected, for example the movement orbit of the X-ray slit beam NB or the movement orbit of the X-ray generator 11 and the X-ray detector 21.

At the step (2050), the slit for a panoramic radiography is selected so as to execute a panoramic radiography with the cassette 22A' and the object "o" to be examined and the support means (rotary arm) 30 are relatively positioned.

At the steps (2060), (2070), a panoramic radiography is executed and the panoramic image is displayed.

The panoramic image is shown on the display means 88 and so on as a scout view.

At the step (2080), an operator designates the interested area "r" on the displayed panoramic image.

At the step (2090), the positional coordinate of the interested area "r" is calculated following the converting regulation step (2040) prepared for the panoramic image obtained by the cassette 22A'.

The step (1100) and thereafter are the same as mentioned above.

This flow chart explains when a panoramic image is obtained as a scout view, however, the procedures are the same when the fluoroscopic image as seen in two-direction is obtained.

In this case, "the cassette 22A" in the steps (1020), (1030), (1050) is changed to "the cassette 22B", "the cassette 22A'" in the steps (2020), (2030), (2050) is changed to "the cassette 22B'", radiography is executed by changing the rotary angle of the support means 30 using each cassette 22, and the interested area "r" is designated on the displayed fluoroscopic image as seen in two-direction.

Figure 9:
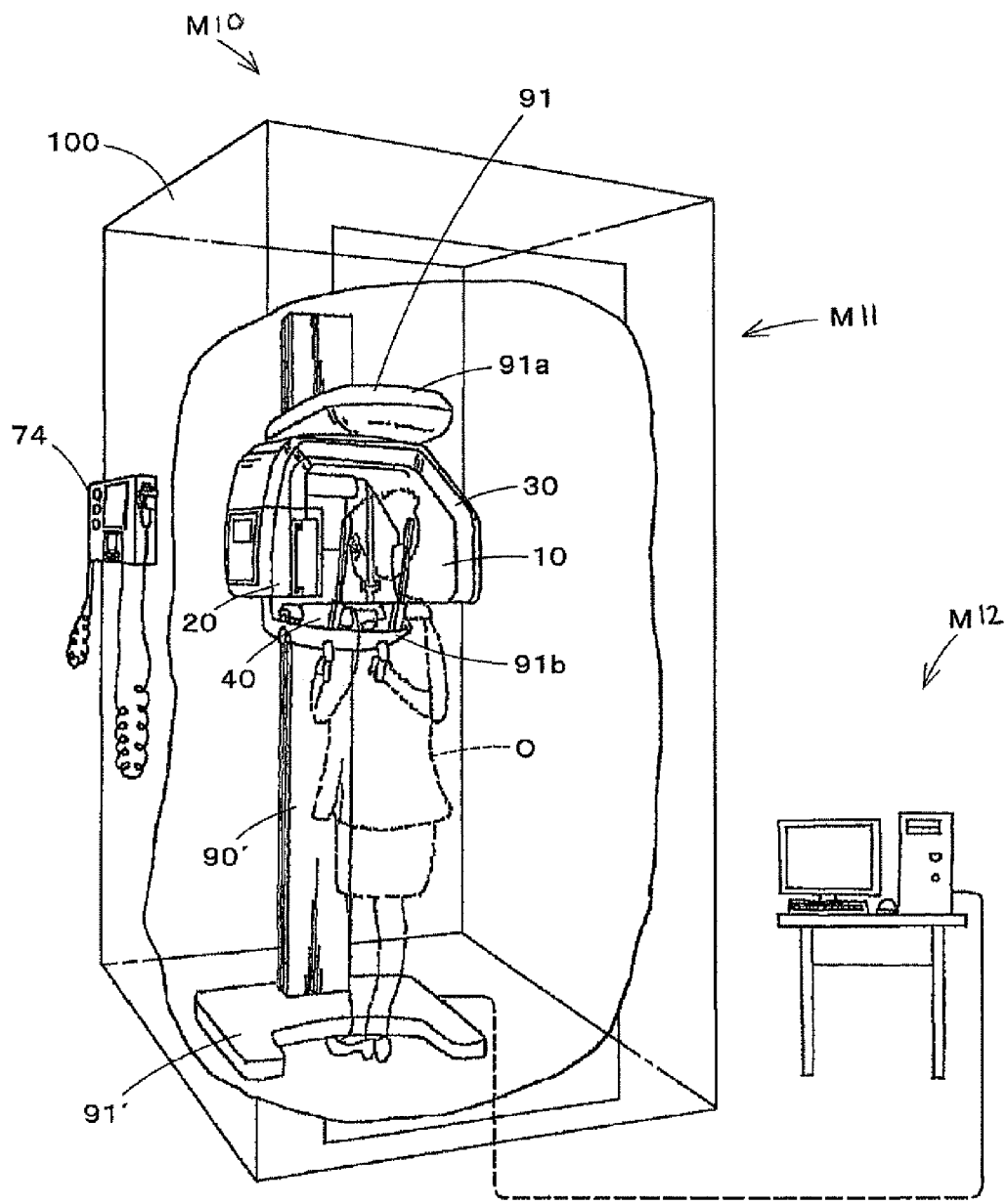
FIG. 9 is a perspective view of other embodiment of an X-ray CT apparatus applied with the present invention.

FIG. 9 shows other embodiment of the X-ray CT apparatus M10 applied with the present invention.

The X-ray CT apparatus main body M11 has the support means 30 which is constructed as a rotary arm including the rotary motor 60r and supports the X-ray generating portion 10 and the X-ray detecting portion 20 at both ends so as to be faced each other, like the X-ray CT apparatus main body M11 shown in FIG. 8a and FIG. 8b.

The elevation frame 91 formed like a letter "C" which projects forward from an upper frame 91a and a lower frame 91b while suspending the support means 30 is provided so as to be movable up and down with respect to a pillar 90' established on a base board 91' by means of an elevation mechanism which is not shown in the figure. The elevation frame 91 includes the XY table 62, not shown, for horizontally moving the rotary axis of the support means 30, like the X-ray CT apparatus main body M11 in FIG. 8a and FIG. 8b.

The lower frame 91b includes the object holding means 40 having an ear rod for fixing a human head being an object "o" to be examined from side to side and a chin rest for fixing the jaw.

The X-ray CT apparatus main body M11 in FIG. 9 is housed in an X-ray shielding room 100 and the operation panel 74 having a compact liquid crystal panel is provided for the outside wall of the room 100 like the X-ray CT apparatus main body M11 shown in FIG. 8a and FIG. 8b.

The X-ray CT apparatus body M11 in FIG. 9 has the X-ray CT image display apparatus M12 to send and receive data therebetween via a communication cable like the X-ray CT apparatus body M11 in FIG. 8a and FIG. 8b.

The invention claimed is:

1. An X-ray CT apparatus having a support means with an X-ray generator and an X-ray detector faced to each other that is relatively rotated around an object disposed between said X-ray generator and said X-ray detector, said X-ray CT apparatus rotating said support means for executing a CT for a local region of said object; and said X-ray CT apparatus further moving said X-ray generator and said X-ray detector along an orbit for a panoramic radiography for executing the panoramic radiography; said apparatus comprising:

an image data input means for taking in attribute information of an X-ray image data outputted from another X-ray apparatus different and external from said X-ray CT apparatus the X-ray image data comprising a panoramic image obtained by a panoramic radiography by said another X-ray apparatus, said attribute information including apparatus type of said another X-ray apparatus, and said orbit of said X-ray CT apparatus for the panoramic radiography being different from an orbit of said another X-ray apparatus for the panoramic radiography;

a display operation means having thereon a specific display area with which an X-ray image data of a panoramic image obtained by said X-ray CT apparatus or said X-ray image data taken from said another apparatus is shown as a scout view and designating an interested area on the displayed area;

a coordinate processing means selecting one of converting regulations for a panoramic image obtained by said X-ray CT apparatus, and selecting another converting regulation for the panoramic image obtained by said another X-ray apparatus with reference to said attribute information corresponding to the type of X-ray apparatus, and converting a two-dimensional position of said designated interested area on said display area into a three-dimensional coordinate information based on said selected another converting regulation; and a position control means for relatively moving said object, to said X-ray generator and said X-ray detector, in order to execute the CT for said local region of said interested area, based on said three-dimensional coordinate information as converted.

2. The X-ray CT apparatus as set forth in claim 1, wherein said display operation means further receives a zoomable operation for said X-ray image data taken from said another apparatus so as to spread said X-ray image data taken from said another apparatus shown as said scout view in a desirable condition relative to said display area for using the converting regulations for the panoramic image obtained by said X-ray CT apparatus as a default converting regulation.

3. The X-ray CT apparatus as set forth in claim 1 or 2, wherein said image data input means further takes an X-ray image data of a fluoroscopic image as seen in two-dimensions of said object to be examined obtained by and outputted from said another X-ray apparatus together with an attribute information of said fluoroscopic image including apparatus type of said another X-ray apparatus, said display operation means shows said X-ray image data of said fluoroscopic image as said scout view, and said coordinate processing means selects one of converting regulations for said fluoroscopic image obtained by said another X-ray apparatus with reference to said attribute information corresponding to the type of X-ray apparatus.

4. The X-ray CT apparatus as set forth in claim 1 or 2, wherein said image data input means is an image data input means for taking in said X-ray image data and said attribute information from said another X-ray apparatus via a removable storage medium.

5. The X-ray CT apparatus as set forth in claim 3, wherein said image data input means is an image data input means for taking in said X-ray image data and said attribute information from said another X-ray apparatus via a removable storage medium.

* * * * *